US006981499B2

(12) United States Patent
Anderson et al.

(10) Patent No.: US 6,981,499 B2
(45) Date of Patent: Jan. 3, 2006

(54) MEDICAMENT DISPENSER

(75) Inventors: Gregor John McLennan Anderson, Ware (GB); Stanley George Bonney, Ware (GB); Anthony Patrick Jones, Ware (GB)

(73) Assignee: Glaxo Group Limited, Greenford (GB)

( * ) Notice: Subject to any disclaimer, the term of this patent is extended or adjusted under 35 U.S.C. 154(b) by 224 days.

(21) Appl. No.: 10/149,238

(22) PCT Filed: Dec. 8, 2000

(86) PCT No.: PCT/EP00/12392

§ 371 (c)(1),
(2), (4) Date: Jun. 7, 2002

(87) PCT Pub. No.: WO01/41849

PCT Pub. Date: Jun. 14, 2001

(65) Prior Publication Data

US 2003/0000524 A1 Jan. 2, 2003

(30) Foreign Application Priority Data

| Dec. 11, 1999 | (GB) | ............................................. 9929281 |
| Feb. 25, 2000 | (GB) | ............................................. 0004359 |
| May 10, 2000 | (GB) | ............................................. 0011124 |
| Oct. 31, 2000 | (GB) | ............................................. 0026648 |

(51) Int. Cl.
*A61M 11/00* (2006.01)

(52) U.S. Cl. ............................. 128/200.23; 128/200.14; 128/203.15

(58) Field of Classification Search ............ 128/200.14, 128/200.23, 204.23, 200.11, 200.12, 200.16, 128/200.18, 203.15, 205.26; 116/308
See application file for complete search history.

(56) References Cited

U.S. PATENT DOCUMENTS

| 4,518,384 A | 5/1985 | Tarello et al. |
| 4,940,966 A | 7/1990 | Pettigrew et al. |
| 5,061,914 A | 10/1991 | Busch et al. |

(Continued)

FOREIGN PATENT DOCUMENTS

| EP | 0 009 291 B1 | 4/1980 |
| EP | 0 009 291 A1 | 4/1980 |
| EP | 0 009 292 A1 | 4/1980 |

(Continued)

OTHER PUBLICATIONS

David L. Brock, "Review of Artificial Muscle based on Contractile Polymers", Massachusetts Institute of Technology Artificial Intelligence Laboratory Memo No. 1330, 15pp., Nov. 1991.

Kwang J. Kim, et al., "Ionic polymer–metal composites: II. Fundamentals", Smart Mater. Struct. 10:4, pp. 819–833, (Aug. 2001).

(Continued)

*Primary Examiner*—Henry Bennett
*Assistant Examiner*—Andrea M. Ragonese
(74) *Attorney, Agent, or Firm*—J. Michael Strickland

(57) ABSTRACT

There is provided a medicament dispenser comprising a medicament container having a dispensing mechanism; a container seat for receipt of the container; an anchor station; and a coupling between said container seat and said anchor station capable on deformation of moving the container seat relative to the anchor station to actuate the dispensing mechanism. The coupling is reversibly deformable in response to the application of non-mechanical energy thereto. The non-mechanical energy may comprise heat energy, electrical current energy, electrical field energy or magnetic field energy.

98 Claims, 10 Drawing Sheets

U.S. PATENT DOCUMENTS

| | | | |
|---|---|---|---|
| 5,201,322 A | 4/1993 | Henry et al. | |
| 5,411,173 A | 5/1995 | Weinstein | |
| 5,415,631 A | 5/1995 | Churinetz et al. | |
| 5,447,150 A | 9/1995 | Bacon et al. | |
| 5,482,032 A | 1/1996 | Smith et al. | |
| 5,497,764 A * | 3/1996 | Ritson et al. | 128/200.14 |
| 5,743,250 A | 4/1998 | Gonda et al. | |
| 5,772,085 A | 6/1998 | Bryant et al. | |
| 5,958,154 A | 9/1999 | O'Handley et al. | |
| 6,036,942 A | 3/2000 | Alband | |
| 6,131,566 A | 10/2000 | Britto | |
| 6,237,590 B1 | 5/2001 | Leedom et al. | |
| 6,475,467 B1 * | 11/2002 | Keller et al. | 424/45 |
| 2002/0189612 A1 | 12/2002 | Rand | |
| 2003/0005926 A1 | 1/2003 | Jones et al. | |
| 2003/0079744 A1 | 5/2003 | Bonney et al | |
| 2004/0025871 A1 | 2/2004 | Davies | |

FOREIGN PATENT DOCUMENTS

| | | |
|---|---|---|
| EP | 0 009 292 A2 | 4/1980 |
| EP | 0 009 293 A1 | 4/1980 |
| EP | 0461281 A | 12/1991 |
| EP | 0 870 699 A2 | 10/1998 |
| WO | WO9013327 A | 11/1990 |
| WO | WO9207599 A | 5/1992 |
| WO | 92/12402 A1 | 7/1992 |
| WO | WO9215353 A | 9/1992 |
| WO | 96/31790 A1 | 10/1996 |
| WO | 99/06091 A1 | 2/1999 |
| WO | 99/36334 A1 | 7/1999 |
| WO | 01/24690 A2 | 4/2001 |
| WO | 01/24690 A3 | 4/2001 |
| WO | 01/26020 A1 | 4/2001 |
| WO | 01/26021 A1 | 4/2001 |
| WO | 01/41846 A1 | 6/2001 |
| WO | 01/41847 A3 | 6/2001 |
| WO | 01/41847 A2 | 6/2001 |

OTHER PUBLICATIONS

Kwang J. Kim, et al., "Ionic polymer–metal composites: II. Manufacturing techniques", Smart Mater. Struct. 12:1, pp. 65–79, (Feb. 2003).

Mohsen Shahinpoor, et al., "Ionic polymer–metal composites (IPMCs) as biometric sensors, actuators, transducers, and artificial muscles –a review", Smart Mater. Struct. 7:6, pp. R15–R30, (Dec. 1998).

M. Shahinpoor and K. J. Kim, "Ionic polymer–metal composites: I. Fundamentals", Smart Mater. Struct. 10:4, pp. 819–833, (Aug. 2001).

M. Shahinpoor and K. J. Kim, "Ionic polymer–metal composites: III. Modeling and simulation as biometric sensors, actuators, transducers, and artificial muscles", Smart Mater. Struct. 13:6, pp. 1362–1388, (Dec. 2004).

M. Shahinpoor and K. J. Kim, "Ionic polymer–metal composites: IV. Industrial and medical applications", Smart Mater. Struct. 14:1, pp. 197–214, (Feb. 2005).

* cited by examiner

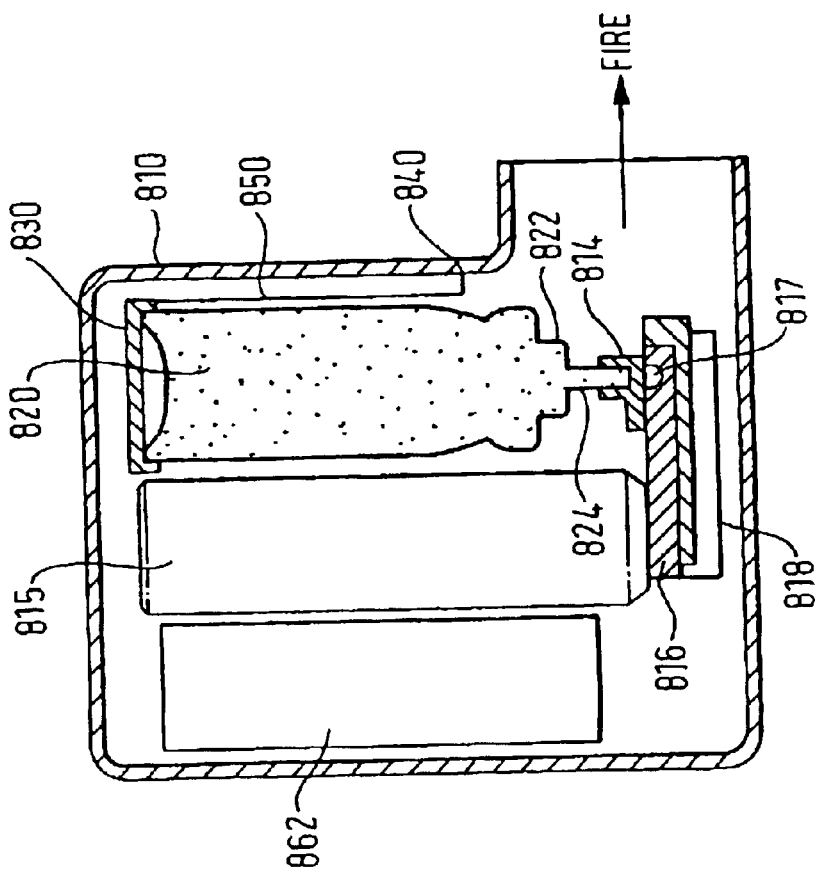
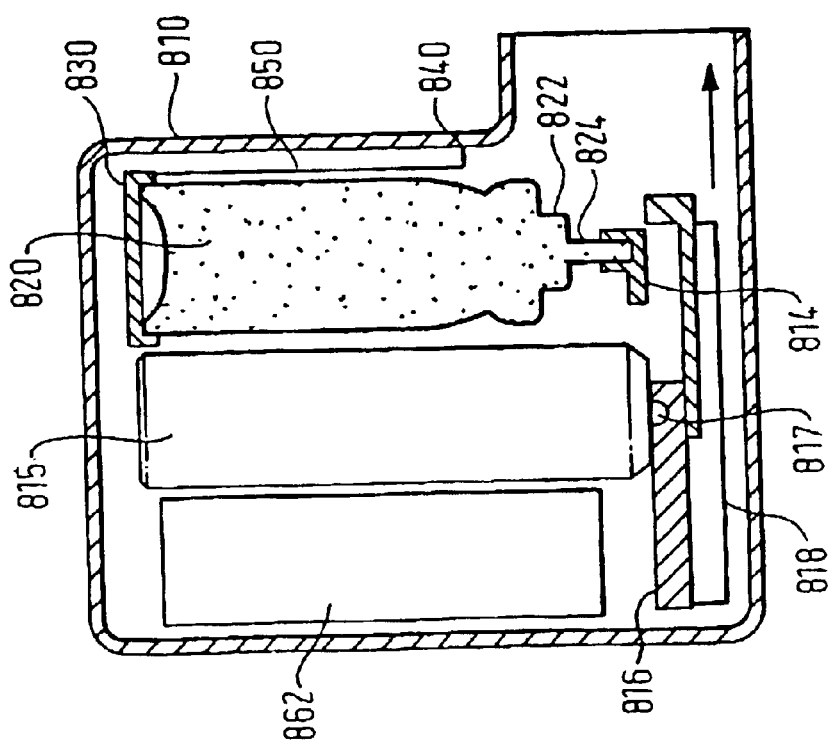
FIG. 9b
FIG. 9a

MEDICAMENT DISPENSER

This application is filed pursuant to 35 USC 371 as a United States National Phase Application of Serial No. PCT/EP00/12392 filed 8 Dec. 2000, which claims priority from GB 9929281.5 filed 11 Dec. 1999, GB 0004359.6 filed 25 Feb. 2000; GB 0011124.5 filed 10 May 2000; and GB 0026648.6 filed 31 Oct. 2000, all in the United Kingdom.

This invention relates to a medicament dispenser including a medicament container having a dispensing mechanism actuable by an actuator. The dispenser is particularly suitable for use as an inhalation device.

It is well known to treat patients with medicaments contained in an aerosol, for example, in the treatment of respiratory disorders. It is also known to use for such treatment, medicaments which are contained in an aerosol and are administered to a patient by means of an inhalation device comprising a tubular housing or sleeve in which the aerosol container is located and an outlet tube leading out of the tubular housing. Such inhalation devices are generally referred to as metered dose inhalers (MDIs). The aerosol containers used in such inhalation devices are designed to deliver a predetermined dose of medicament upon each actuation by means of an outlet valve member at one end which can be opened either by depressing the valve member while the container is held stationary or by depressing the container while the valve member is held stationary. In the use of such devices, the aerosol container is placed in the tubular housing with the outlet valve member of the container communicating via a support with the outlet tube, for example a nozzle or mouthpiece. When used for dispensing medicaments, for example in bronchodilation therapy, the patient then holds the housing in a more or less upright condition and the mouthpiece or nozzle of the inhalation device is placed in the mouth or nose of the patient. The aerosol container is pressed towards the support to dispense a dose of medicament from the container which is then inhaled by the patient.

It is also known to use dry powder inhalation devices for the delivery of inhalable medicament. In one aspect, such dispensers comprise pre-metered doses of powdered medicament, for example in capsules or blisters. In another aspect, such dispensers comprise a reservoir of powdered medicament from which doses are metered prior to or concurrent with the delivery process. In either case, the device may be designed for passive release of medicament, where the medicament is simply made available at a delivery position for aerosolisation in response to the inhalation of the patient. Alternatively, an active release mechanism may be used whereby a 'puff' of gas or air is provided to the delivery position to assist in aerosolisation of the powder prior to or concurrent with the inhalation of the patient. Such devices are generally called active release dry powder inhalers (active DPIs). The source of the compressed gas or air is generally an aerosol container but can also be provided by another suitable means such as a pump or plunger mechanism.

It is also well known to use syringes for the delivery of injectable medicament to a patient. Traditional syringes rely on puncturing of the patient's skin by a hollow needle through which the injectable medicament (in solution or suspension form) is delivered to the muscle or tissue of the patient. Recently developed needleless systems for the delivery of injectables employ high velocity injection of particle formulated drugs or vaccine through the skin and into any physically accessible tissue. Other needleless systems employ similar high velocity injection of drug or vaccine coated on to a suitable carrier particle. Such needleless systems may be configured to include a source of compressed air or gas, which on release provides energy to propel the medicament particles for injection into the skin.

It may be understood that effective delivery of medicament to the patient using an inhalation device such as an MDI or active DPI as described above is to an extent dependent on the patient's ability to manually actuate the device (e.g. firing of the aerosol) and to co-ordinate the actuation thereof with the taking of a sufficiently strong inward breath. For some patients, particularly young children, the elderly and the arthritic, manual actuation of the device can present difficulties. Other patients find it difficult to co-ordinate the taking of a reliable inward breath with actuation of the device. Both of these sets of patients run the risk that they do not receive the appropriate dose of medicament.

It may also be understood that effective delivery of medicament to the patient using a syringe or needleless injection system as described above also requires care and dexterity.

The Applicants have now developed a medicament dispenser which does not require controlled manual actuation by the patient. In one aspect, the dispenser comprises a medicament container having a dispensing mechanism such as a valve or plunger and an actuator for actuating the dispensing mechanism. In another aspect, the device comprises an active DPI or needless injection system having a source of compressed air or gas having a dispensing mechanism such as a valve or plunger and an actuator for actuating the dispensing mechanism. Actuation is responsive to the application of non-mechanical energy to a coupling element of the actuator. The non-mechanical energy can be in the form of heat provided by electrical current flow through the coupling element, which in turn can be provided in response to the sensing of the breath of a patient. Alternatively, the non-mechanical energy can be in the form of a magnetic field provided by a suitable magnetic field source such as a permanent magnet or an electromagnet.

U.S. Pat. No. 5,061,914 describes a shape memory alloy micro-actuator. The actuator comprises a nickel-titanium alloy material which undergoes a temperature induced phase transition when heated. The phase transition results in contraction of the actuator. The actuator can be mechanically coupled to a micro-mechanical element for motion thereof.

U.S. Pat. No. 5,958,154 describes alloy materials which undergo a phase transition in response to the application of a magnetic field.

According to one aspect of the present invention there is provided a medicament dispenser comprising a housing; a medicament container having a dispensing mechanism; a container seat for receipt of the container; an anchor station on the housing or connecting therewith; and a coupling between said container seat and said anchor station capable on deformation of moving the container seat relative to the anchor station to actuate the dispensing mechanism. The coupling is reversibly deformable in response to the application of non-mechanical energy thereto.

According to another aspect of the present invention there is provided a medicament dispenser comprising a medicament container having a dispensing mechanism; a container seat for receipt of the container; a dispenser seat for receipt of the dispensing mechanism; and a coupling between said container seat and said dispenser seat capable on deformation of moving the container seat relative to the dispenser seat to actuate the dispensing mechanism. The coupling is reversibly deformable in response to the application of non-mechanical energy thereto.

According to a further aspect of the present invention there is provided a medicament dispenser comprising a housing; a medicament container for containing medicament for release; an aerosol container having a dispensing mechanism; a container seat for receipt of the aerosol container; an anchor station on the housing or connecting therewith; and a coupling between said container seat and said anchor station capable on deformation of moving the container seat relative to the anchor station to actuate the dispensing mechanism to energise released medicament, wherein the coupling is reversibly deformable in response to the application of non-mechanical energy thereto.

According to a further aspect of the present invention there is provided a medicament dispenser comprising a medicament container for containing medicament for release; an aerosol container having a dispensing mechanism; a container seat for receipt of the container; a dispenser seat for receipt of the dispensing mechanism; and a coupling between said container seat and said dispenser seat capable on deformation of moving the container seat relative to the dispenser seat to actuate the dispensing mechanism to energise released medicament, wherein the coupling is reversibly deformable in response to the application of non-mechanical energy thereto.

Suitably, in accord with the two aspects introduced directly above, the medicament container comprises a release mechanism for releasing medicament therefrom, such as a valve or other suitable mechanism which may also provide a metering function. In another aspect, the medicament container may be arranged for rupture in response to firing of the aerosol container, thereby making the medicament contents thereof available for energisation. In one aspect, the medicament dispenser is in the form of an active DPI in which a 'puff' of air or gas (e.g. helium) is delivered from an aerosol container, pump or plunger mechanism to aerosolise a dose of released dry powder medicament. In another aspect, the medicament dispenser is in the form of a needless injection system in which compressed air or gas (e.g. helium) is delivered at high velocity from the aerosol container to propel a dose of dry powder medicament for injection into the skin. Thus, suitably the aerosol container, which as used herein refers to any suitable container for comprising liquefied gas under pressure, comprises a compressed air or gas (e.g. helium).

The release mechanism comprises means for the making medicament available from the medicament container for release to the patient. The release may be active in the sense that medicament is actively dispensed from the container, or the release may be passive in the sense that medicament is merely made available for release when the release means is actuated. Release may be to a delivery position for delivery to the patient, or alternatively there may be a further transport step in which the medicament is transported from a non-delivery, position, to a position where the drug is ready for delivery to the patient.

In one aspect, the medicament is pre-metered prior to release. For example, the medicament is pre-metered in capsules, strip or tape form.

In another aspect, the medicament container comprises a reservoir for medicament (e.g. in powder form) and a meter is provided for metering an amount (e.g. by volume or by weight) of medicament from said reservoir.

Suitably, the dispensing mechanism is selected from the group consisting of a valve, pump or plunger mechanism. Preferably, the dispensing mechanism comprises a metering mechanism.

In one aspect, the dispensing mechanism comprises a valve. Suitably, the valve is a slide valve. Other valve systems include, but are not limited to, poppet valve systems, wedge gate valve systems, double-disc gate valve systems, globe and angle valve systems, swing check valve systems, end cock valve systems, and other like valve systems. The valve design is typically a function of providing a predetermined dosage or amount of the medicament contained within the container to a user.

Where the medicament container is a pressurized aerosol container, the valve typically comprises a valve body having an inlet port through which a medicament aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 $\mu$l, such as 25 $\mu$l, 50 $\mu$l or 63 $\mu$l. Suitably, the valve body defines a metering chamber for metering an amount of medicament formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of medicament formulation into the metering chamber.

The valve may also comprise a 'free flow aerosol valve' having a chamber and a valve stem extending into the chamber and movable relative to the chamber between dispensing and non-dispensing positions. The valve stem has a configuration and the chamber has an internal configuration such that a metered volume is defined therebetween and such that during movement between is non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation. A valve of this type is described in U.S. Pat. No. 5,772,085.

The valve may also have a structure and action similar to those aerosol valves described in European Patent Application No. EP-A-870,699 and PCT Patent Application No. WO99/36334.

In another aspect, the dispensing mechanism comprises a plunger, such as might exist in a syringe for the delivery of injectable medicament to a patient. Embodiments including multiple plungers and multiple syringe chambers are also envisaged. The syringe contents may for example, be liquid, solutions, suspensions, particulates or in freeze-dried form. A retract or reset mechanism is typically provided for the plunger.

Traditional syringes rely on puncturing of the patient's skin by a hollow needle through which the injectable medicament (in solution or suspension form) is delivered to the muscle or tissue of the patient. Recently developed needleless systems for the delivery of injectables employ high velocity injection of particle formulated drugs or vaccine through the skin and into any physically accessible tissue. Other needleless systems employ similar high velocity injection of drug or vaccine coated on to a suitable carrier particle.

In another aspect, the dispensing mechanism comprises a pump mechanism such as might be found in a dispenser for dispensing liquid or solution (e.g. aqueous solution) form medicament. The pump may deliver the medicament directly to the patient (e.g. as a nasal spray) or the pump may deliver the medicament to an intermediate position at which further energy is supplied thereto to further propel, aerosolise or otherwise direct the medicament dose to the patient.

A reset mechanism may be provided for resetting the dispensing mechanism after actuation thereof. The reset mechanism may for example, comprise a spring, motor, mechanical arrangement or a reset coupling which is reversibly deformable in response to the application of non-mechanical energy thereto.

The term 'non-mechanical energy' herein is used to mean essentially any energy type which is not mechanical energy. The coupling and any reset coupling herein typically comprise a material which deforms, or undergoes a phase transition in response to the application of non-mechanical energy, thereby resulting in a change in shape/dimension of the coupling which serves to actuate the dispensing mechanism. In embodiments the energy may be in the form of heat energy, electrical current energy, electrical field energy and magnetic field energy.

Preferably, the non-mechanical energy comprises electric current flow through the coupling or reset coupling.

Preferably, the coupling or reset coupling comprises a wire, strip, coil or tube.

Arrangements comprising multiple strips, wires, coils, or tubes are also envisaged. The multiple strips, wires, coils, or tubes may be arranged in any suitable fashion including parallel or series arrangements and bundle arrangements.

The coupling may be coated with any suitable coating, or encased within any suitable encasing including a shrink-wrap sheath.

In one particular aspect, the coupling or reset coupling comprises one or more wires which contract in response to application of non-mechanical energy thereto.

Preferably, the degree of contraction of the coupling is from 2% to 8%.

In embodiments, the coupling comprises an alloy which undergoes a phase transition on heating (shape memory alloys). Certain shape memory alloys also undergo a change in shape on recooling without externally applied energy. Such two way shape memory alloys are also envisaged for use herein.

In one embodiment, the shape memory alloy is preferably a nickel-titanium alloy such as a nickel-titanium alloy comprising from 5% to 95%, preferably from 20% to 80%, nickel by weight and from 95% to 5%, preferably from 80% to 20%, titanium by weight. By nickel-titanium alloy it is meant an alloy comprised essentially of nickel and titanium, although other elements such as Cu and Nb may be present in small (e.g. trace) amounts.

In other embodiments, the shape memory alloy is preferably a copper-aluminum-nickel alloy or a copper-zinc-aluminum alloy. Trace amounts of other elements may also be present.

In further embodiments, the coupling comprises an alloy which undergoes a phase transition on application of a magnetic field thereto (magnetic shape memory alloys). These materials are generally intermetallic, ferromagnetic alloys that exhibit twin variants in the martensitic, or low-temperature, phase of the material. Suitable magnetic shape memory alloys are for example, described in U.S. Pat. No. 5,958,154.

In one embodiment, the magnetic shape memory alloy exhibits an austenitic crystal structure above a characteristic phase transformation temperature and also exhibits a martensitic twinned crystal structure below the phase transformation temperature. The alloy has a magnetocrystalline anisotropy energy that is sufficient to enable motion of twin boundaries of the martensitic twinned crystal structure in response to application of a magnetic field to the martensitic twinned crystal structure.

Where a magnetic shape memory alloy is employed the medicament dispenser preferably includes a magnetic field source disposed with respect to the coupling in an orientation that applies to the coupling a magnetic actuation field in a direction that is substantially parallel with a selected twin boundary direction of the martensitic twinned crystal structure of the coupling material.

Alternatively, the medicament dispenser preferably includes a magnetic bias field source disposed with respect to the coupling in an orientation that applies a magnetic bias field to the coupling, and a magnetic actuation field source disposed with respect to the coupling in an orientation that applies a magnetic actuation field to the coupling material in a direction that is substantially perpendicular to the orientation of the applied magnetic bias field.

A preferred magnetic shape memory alloy is the actuator material comprising an alloy composition defined as $Ni_{65-x-y}Mn_{20}+xGa_{15}+y$, where x is between 3 atomic % and 15 atomic % and y is between 3 atomic % and 12 atomic %. Preferably, the actuator material comprises an alloy composition defined as $Ni_{65-x-y}Mn_{20}+xGa_{15}+y$, where x is between 6 atomic % and 10 atomic % and y is between 5 atomic % and 9 atomic %; or where x is between 12 atomic % and 15 atomic % and y is between 3 atomic % and 6 atomic %; or where x is between 10 atomic % and 14 atomic % and y is between 3 atomic % and 6 atomic %; or where x is between 7 atomic % and 11 atomic % and y is between 3 atomic % and 7 atomic %. In a particularly preferred aspect, the alloy is $Ni_{50}Mn_{25}Ga_{25}$.

Another preferred magnetic shape memory alloy is the alloy having the composition $(Ni_aFe_bCo_c)_{65-x-y}(Mn_dFe_eCo_f)_{20}+x(Ga_gSi_hAl_i)_{15}+y$, where x is between 3 atomic % and 15 atomic % and y is between 3 atomic % and 12 atomic %, and where a+b+c=1, where d+e+f=1, and g+h+i=1.

In preferred aspects, b is between zero and 0.6, c is between zero and 0.6, and e, f, h and i are each zero; or b and c are each zero, e is between zero and 0.6, f is between zero and 0.6, and h and i are each zero; or b, c, e and f are each zero, h is between zero and 0.5, and i is between zero and 0.5.

Other suitable shape memory alloys include those based on ion-exchange polymer composites such as are described in 'Ionic Polymer-Metal Composites (IPMC) As Biomimetic Sensors, Actuators & Artificial Muscles—A Review', M. Shahinpoor, Y. Bar-Cohen, J. O. Simpson and J. Smith as published at http://www.unm.edu/~amri/paper.html.

Other potentially suitable shape memory alloys include those based on contractile polymers such as are described in 'Review of Artificial Muscle based on Contractile Polymers', Massachusetts Institute of Technology Artificial Intelligence Laboratory Memo No. 1330, November 1991, David L. Brock.

Preferably, the one or more wires have a diameter from 30 to 400 micrometers, preferably from 50 to 150 micrometers.

Preferably, the coupling comprises from two to twenty, preferably six to twleve wires which contract in response to the application of non-mechanical energy thereto. The wires may be arranged in any suitable fashion including parallel or series arrangements and bundle arrangements.

In another aspect, the coupling comprises a strip which comprises multiple layers of different metals. Suitable strips typically comprise a plurality of layers of material, each material having a different coefficient of thermal expansion.

Preferred examples of strips include those comprising multiple layers of different metals (e.g. bimetallic strips) and strips comprising at least one piezoelectric material. Suitable piezoelectric materials include piezoelectric ceramics, such as compounds of lead zirconate and lead titanate, and piezoelectric crystals which are generally polycrystalline ferroelectric materials with the perovskite structure. Such piezoelectric materials generally deform in response to the application of an electric field.

In one aspect, the coupling is deformable in response to heating arising from electrical current flow in the range from 0.01A to 100A, preferably from 0.1A to 5A.

In another aspect, the coupling is deformable in response to the application of an electrical field, particularly where the coupling comprises a piezoelectric material.

In a further aspect, the coupling is deformable in response to a magnetic field of from 0.01 to 100 Tesla. The magnetic field may for example, be produced by a permanent magnet or by an electromagnet.

Preferably, the medicament dispenser additionally comprises an electrical energy source for providing electric current, or for providing an electric field, or for powering an electromagnet to provide a magnetic field. In one aspect, the electrical energy source comprises a voltaic cell or battery of voltaic cells which may be rechargeable. In another aspect, the electrical energy source comprises a photovoltaic cell or battery of photovoltaic cells. In a further aspect, the electrical energy source comprises a converter for converting mechanical energy into electrical energy. In a further aspect, the electrical energy source comprises a capacitor for local storage of charge. Suitable capacitors comprise those known as 'super capacitors' with a high capacitance to size ratio, such as those consisting of solid electrodes and liquid electrolyte.

Any known systems for power management and conservation may be employed with the electrical energy source to manage and/or conserve the power output thereof.

Energy may be conserved by a variety of means to enable the device to operate for longer on a given source of energy, such as a battery. Energy conservation or saving methods have additional advantages in terms of reducing the size requirements of the power source (e.g. battery) and thus the weight and portability of the inhalation device.

A variety of energy saving methods are available which generally involve reducing power consumption. One such method is to use a clock or timer circuit to switch the power on and off at regular or predetermined intervals. In another method the system can selectively switch on/off specific electronic devices, such as visual display units or sensors, in order to power these devices only when they are required to perform a particular sequence of events. Thus different electronic devices may be switched on and off at varying intervals and for varying periods under control of the system. The power sequencing system may also respond to a sensor, such as a motion or breath sensor, which is activated on use of the device.

Low power or "micropower" components should be used within the electronics where possible and if a high power device is required for a particular function this should be put into a low power standby mode or switched off when not required. Similar considerations apply in the selection of transducers. Operation at low voltage is desirable since power dissipation generally increases with voltage.

For low power digital applications complementary metal oxide semi-conductor (CMOS) devices are generally preferred and these may be specially selected by screening for low quiescent currents. Clock speeds of processors and other logic circuits should be reduced to the minimum required for computational throughput as power consumption increases with frequency. Supply voltages should also be kept at minimal values consistent with reliable operation because power dissipation in charging internal capacitance's during switching is proportional to the square of the voltage. Where possible, supply voltages should be approximately the same throughout the circuit to prevent current flowing through input protection circuits. Logic inputs should not be left floating and circuits should be arranged so that power consumption is minimised in the most usual logic output state. Slow logic transitions are undesirable because they can result in relatively large class-A currents flowing. Resistors may be incorporated in the power supply to individual devices in order to minimise current in the event of failure.

In some control applications, devices that switch between on and off states are preferred to those that allow analog (e.g. linear) control because less power is dissipated in low resistance on states and low current off states. Where linear components are used (e.g. certain types of voltage regulators) then types with low quiescent currents should be selected. In some circuit configurations it is preferable to use appropriate reactive components (i.e. inductors and capacitors) to reduce power dissipation in resistive components. Any electrical circuit may incorporate voltage amplification means for generating a higher voltage than that supplied by the voltaic cell or battery of voltaic cells, for example a step-up or inverting switching circuit or a dc-dc converter incorporating an oscillator, transformer and rectifier.

The electrical circuit may incorporate one or more energy storage components such as capacitors or inductors in order to supply a high enough instantaneous current to raise the temperature of the strips or wires at the required rate to the required temperature.

The input to the electrical circuit may be connected to the electrical energy source by means of a mechanical, electromechanical or electronic switching component.

The output of the electrical circuit may be connected to the strips or wires or to an electromagnet by means of a mechanical, electromechanical or electronic switching component or by a component allowing the output current to be controlled in a linear or digital (e.g. pulse width modulated) manner.

Suitable control profiles (e.g. via pulse width modulation) include those where the temperature of a shape memory alloy coupling is initially raised to a holding temperature (H) which is just below the transition temperature (T). Actuation of the coupling is then achievable by heating the coupling to a temperature (A) just above the transition temperature. This can be achieved rapidly because the holding temperature (H) is close to the transition temperature (T). When the source of heating is switched off, deactuation also occurs rapidly because the cooling from a temperature (A) only just above the transition temperature (T) to the transition temperature involves only a small temperature decrease.

The strip or wire components may be powered from the battery using a switching component without additional power supply circuitry.

Suitably, the medicament dispenser additionally comprises a controller for controlling the amount of electrical current flow through the coupling or to an electromagnet.

Suitably, the medicament dispenser additionally comprises a timer for controlling the duration of electrical current flow through the coupling or to an electromagnet.

Suitably, the medicament dispenser additionally comprises a local electrical store such as a capacitor or inductor.

Suitably, the medicament dispenser is provided with a manual override to enable actuation of the device in the event of loss of electrical power.

Suitably, the medicament dispenser is provided with child-resistance features to prevent undesirable actuation thereof by a young child.

In one aspect, the container is an aerosol container, preferably comprising a metering valve at the dispensing outlet. In another aspect, the container is for medicament in solution form (e.g aqueous solution) comprising a pump dispensing mechanism.

In one aspect, the aerosol container comprises a suspension of a medicament in a propellant. The propellant preferably comprises liquefied HFA134a, HFA-227, helium or carbon dioxide.

In another aspect, the aerosol container comprises a solution of a medicament in a solvent.

The medicament is preferably selected from the group consisting of albuterol, salmeterol, fluticasone propionate, beclomethasone dipropionate, salts or solvates thereof and any mixtures thereof. Alternatively, the dispenser may be employed for dispensing vaccine.

Preferably, the valve is a slide valve.

Preferably, the valve is a metering valve. In alternative embodiments, metering of medicament dose may be achievable by pulsing electrical current flow through the coupling or to the electromagnet for a selected dispensing time.

Preferably, the container seat is shaped for snug receipt of the base of the medicament container or aerosol container. Preferably, the dispenser seat is shaped for snug receipt of the tip of the dispensing mechanism. More preferably, the dispenser seat is further shaped to support the walls of the medicament container or aerosol container. Most preferably, the container seat and dispenser seat in combination form a cradle for the medicament container or aerosol container.

Preferably, the container seat and dispenser seat comprise electrically conducting material and the container is electrically insulated therefrom.

In one aspect, the dispensing mechanism comprises an electrically insulating material.

In another aspect, the dispensing mechanism comprises an electrically conducting material and an insulator is provided between the dispensing mechanism and the dispenser seat.

Preferably, deformation of the coupling and hence, actuation of the dispensing mechanism is responsive to a patient-actuable trigger.

In one aspect, said trigger comprises a button, switch or lever arrangement.

In another aspect, the medicament dispenser is in the form of an inhaler for the delivery of inhalable medicament. Inhalation may be through the nose or the mouth. Preferably, deformation of the coupling and hence, actuation of the dispensing mechanism is responsive to a patient-actuable trigger comprising a sensor which senses the breath of a patient. The deformation of the coupling (e.g. by electrical current flow therethrough) may be responsive to the detection of the inward breath of a patient. Alternatively, deformation of the coupling (e.g. by electrical current flow therethrough) may be responsive to a trigger coupled to any point in the breathing pattern of the patient, such as the end of the outward breath.

In one aspect, the sensor comprises a breath-movable element which is movable in response to the breath of a patient. Preferably, the breath-movable element is selected from the group consisting of a vane, a sail, a piston, a diaphragm and an impeller.

Movement of the breath-movable element may be detectable by any suitable technique for detecting movement. Suitable techniques include optical detectors, magnetic detectors or detectors using detection of capacitative effects.

Optical detectors may be used to detect movement of the breath-movable element by providing the element with a patterned outer surface, for example strips in a barcode type arrangement, and locating the optical detector so that it points towards the patterned surface. Movement of the breath-movable element alters the amount of the light source which reflects back onto the optical detector as the beam passes over the patterned surface. The strips may be arranged so that the direction of movement of the element can be detected.

Magnetic detectors may be used to detect the movement of breath-movable element by the use of a magnetic switch device. A reader is located on the dispenser and magnetic material embedded within the breath-movable element (or vice-versa). Movement of the breath-movable element results in a change of the magnetic field experienced by the reader. Alternatively, a Hall effect device can be used whereby a semiconductor measures the strength of the magnetic field of the magnetic material on the breath-movable element.

Detection of capacitative effects may be used to detect movement of the breath-movable element by adding a conductive part to the element and also to a second fixed part of the dispenser. Movement of the breath-movable element results in a change in capacitance which can be measured.

In another aspect, the sensor comprises a pressure sensor for sensing the pressure profile associated with the breath of a patient. A pressure transducer is an example of a suitable pressure sensor.

In another aspect, the sensor comprises an airflow sensor for sensing the airflow profile associated with the breath of a patient.

In another aspect, the sensor comprises a temperature sensor for sensing the temperature profile associated with the breath of a patient.

In another aspect, the sensor comprises a moisture sensor for sensing the moisture profile associated with the breath of a patient.

In another aspect, the sensor comprises a gas sensor for sensing the oxygen or carbon dioxide profile associated with the breath of a patient. The chemical profile of the inhaled and exhaled part of the breath cycle varies and this further may be used as a measurement tool.

Suitably, the breath data includes breath cycle data, FEV, and/or peak flow data.

In one aspect, the coupling is exposable to the airflow arising from the inhalation or expiration of the patient to assist in the cooling of the coupling post-actuation of the dispensing mechanism. Other active cooling mechanisms may be employed, such as fan cooling.

Preferably the medicament dispenser comprises an actuation or dose counter for counting the number of actuations of the dispensing mechanism or releases of dose therefrom. The actuation or dose counter may be mechanical or electronic. More preferably the actuation or dose counter is independent of the coupling so that counting will occur even if the dispensing mechanism is manually actuated.

Preferably a manual override is provided to enable manual actuation of the dispensing mechanism. The manual override may be designed to cover all situations in which the coupling does not actuate in the normal manner. These will include situations where actuation does not happen (e.g. due to power failure). Alternatively, this will include situations where actuation occurs, but reset of the coupling fails (e.g. due to power being in a 'continuous on' mode) and a manual reset, decoupling (e.g. by severing the coupling) or 'circuit break' is employed.

Suitably, the medicament dispenser additionally comprises an electronic data management system. The electronic data management system has input/output capability and comprises a memory for storage of data; a microprocessor for performing operations on said data; and a transmitter for transmitting a signal relating to the data or the outcome of an operation on the data.

Suitably, the electronic data management system comprises an electronic control system for controlling the supply of energy to the coupling. Thus, in aspects the control system may regulate flow of electrical current to the coupling or to any heater or electromagnet source associated therewith.

The control system may form part of a larger electronic data management system capable of receiving inputs from other electronic components. In particular, inputs may be received from any sensor to enable actuation of the coupling in response to sensor, particularly breath sensor input.

The control system may be arranged to accomplish any suitable control of actuation of the coupling including varying the amount of energy supplied thereto, the rate of energy supplied thereto, pulsing patterns of energy supply to the coupling, and more complex control patterns.

Suitably, the electronic data management system is arranged to be responsive to or activated by the voice of a user. Thus, for example the system may be switched on or off in response to a voice command.

The electronic data management system may be integral with the body. Alternatively, the electronic data management system forms part of a base unit which is reversibly associable with the body.

Suitably, the medicament dispenser additionally comprises a data input system for user input of data to the electronic data management system. Preferably, the data input system comprises a man machine interface (MMI) preferably selected from a keypad, voice or noise recognition interface, graphical user interface (GUI) or biometrics interface.

Suitably, the system additionally comprises a visual display unit for display of data from the electronic data management system to the user. The display may for example, comprise a screen such as an LED or LCD screen. More preferably the visual display unit is associable with the housing. More basic display units are envisaged also including those in which a light or pattern of lights is employed to act as a signal to the patient.

The electronic data management system may further comprise a voice synthesiser for verbal communication of data, instructions and feedback to a user.

Suitably, the medicament dispenser additionally comprises a datalink for linking to a local data store to enable communication of data between the local data store and the electronic data management system. The datastore may also comprise data management, data analysis and data communication capability.

The datastore may itself form part of a portable device (e.g. a handheld device) or it may be sized and shaped to be accommodated within the patient's home. The datastore may also comprise a physical storage area for storage of replacement medicament containers. The datastore may further comprise a system for refilling medicament from a reservoir of medicament product stored therewithin. The datastore may further comprise an electrical recharging system for recharging any electrical energy store on the medicament dispenser, particularly a battery recharging system.

The datalink may for example enable linking with a docking station, a personal computer, a network computer system or a set-top box by any suitable method including a hard-wired link, an infra red link or any other suitable wireless communications link.

Suitably, the medicament dispenser additionally comprises an actuation detector for detecting actuation of the dispensing mechanism wherein said actuation detector transmits actuation data to the electronic data management system.

The medicament dispenser may additionally comprise a safety mechanism to prevent unintended multiple actuations of the dispensing mechanism. The patient is thereby protected from inadvertently receiving multiple doses of medicament in a situation where they take a number of short rapid breaths. More preferably, the safety mechanism imposes a time delay between successive actuations of the release means. The time delay is typically of the order of from three to thirty seconds.

Suitably, the medicament dispenser additionally comprises a release detector for detecting release of medicament from the medicament container, wherein said release detector transmits release data to the electronic data management system.

Suitably, the medicament dispenser additionally comprises a shake detector for detecting shaking of the medicament container (e.g. prior to actuation of the dispensing mechanism), wherein said shake detector transmits shake data to the electronic data management system.

Suitably, any actuation detector, release detector or shake detector comprises a sensor for detecting any suitable parameter such as movement. Any suitable sensors are envisaged including the use of optical sensors. The release detector may sense any parameter affected by release of the medicament such as pressure, temperature, sound, moisture, carbon dioxide concentration and oxygen concentration.

Suitably, the medicament dispenser additionally comprises a breath trigger for triggering the dispensing mechanism, said breath trigger being actuable in response to a trigger signal from the electronic data management system. Preferably, the electronic data management system includes a predictive algorithm or look-up table for deriving from the breath data when to transmit the trigger signal. For example, a real-time analysis of the patient breath waveform may be made and the trigger point derived by reference to that analysed waveform.

Suitably, the electronic data management system includes a predictive algorithm or look-up table for calculating the optimum amount of medicament to dispense.

Suitably, the memory on the electronic data management system includes a dose memory for storing dosage data and reference is made to the dose memory in calculating the optimum amount of medicament to dispense.

Suitably, the medicament dispenser additionally comprises a selector for selecting the amount of medicament to dispense from said dispensing mechanism. In one aspect, the selector is manually operable. In another aspect, the selector is operable in response to a signal from the transmitter on the electronic data management system.

Suitably, the medicament dispenser comprises in association with a body or housing thereof, a first transceiver for transmitting and receiving data and in association with the medicament container, a second transceiver for transmitting and receiving data, wherein data is transferable in two-way fashion from the first transceiver to the second transceiver. The data is preferably in digital form and suitable for transfer by electronic or optical means. A medicament dispenser of this general type is described in pending UK Patent Application No. 0020538.5.

The body or housing of the medicament dispenser is typically shaped to define a cavity within which the medicament container is receivable. The body and/or medicament container may be further shaped with any manner of grooves, indentations or other shaping or surface details to define a 'lock and key' relationship between the body and the container. Colour guides, arrows and any other surface markings may also be employed.

One advantage of embodiments of this type is the ability to store many types of information in different parts of the memory structure of the transceivers. The information is furthermore stored in a form which is readily and accurately transferable. The information could for example, include manufacturing and distribution compliance information written to the memory at various points in the manufacturing or distribution process, thereby providing a detailed and readily accessible product history of the dispenser. Such product history information may, for example, be referred to in the event of a product recall. The compliance information could, for example, include date and time stamps. The information could also include a unique serial number stored in encrypted form or in a password protectable part of the memory which uniquely identifies the product and therefore may assist in the detection and prevention of counterfeiting. The information could also include basic product information such as the nature of the medicament and dosing information, customer information such as the name of the intended customer, and distribution information such as the intended product destination.

On loading or reloading the dispenser with a medicament container (such as an aerosol canister or dry powder cassette) the second transceiver may, for example, read the unique serial number, batch code and expiry date of the medicament and any other information on the second transceiver. In this way the nature and concentration of the medicament, together with the number of doses used or remaining within the container, may be determined. This information can be displayed to the patient on a visual display unit. Other information, such as the number of times the dispenser has been reloaded with a medicament container, may also be displayed.

Similarly, should the container be removed from the housing before the supply of medicament is exhausted, the same data can be read from the second transceiver and the number of doses remaining or used determined. Other information, such as the date and time of administration of the drug, or environmental exposure data such as the minimum / maximum temperatures or levels of humidity the medicament container has been exposed to, may also be read and displayed to the user.

In the event that the supply of medicament within the container becomes exhausted, or that the shelf life of the medicament has expired, or that the first transceiver does not recognise the batch code on the second transceiver, activation of the dispenser may be prevented to safeguard the user. Activation may also be prevented if the medicament has been exposed to extreme environmental conditions for periods out with the manufacturer's guidelines.

Data may be transferred to and from any transceiver during the period of use of the medicament dispenser by the patient. For example, the medicament dispenser may include an electronic data management system having various sensors associated therewith. Any data collected by the sensors or from any data collection system associated with the electronic data management system including a clock or other date/time recorder is transferable.

Data may be transferred each time the patient uses the device. Or alternatively, data may be stored in a database memory of the electronic data management system and periodically downloaded to any transceiver. In either case, a history of the usage of the device may be built up in the memory of a transceiver.

In one embodiment herein, a history of the usage of the medicament dispenser is transferred to the second transceiver on the aerosol container. When the medicament container is exhausted it is exchanged by the patient for a new refill container. At the point of exchange, which will typically occur at the pharmacy, data may be transferred from the exhausted container to the refill and vice-versa. Additionally, usage history data may be read from the refill and transferred to a healthcare data management system for example comprising a network computer system under the control of a healthcare data manager.

Methods are envisaged herein whereby the patient is given some sort of reward for returning the refill and making available the data comprised within the second transceiver. Methods are also envisaged herein whereby the healthcare data manager is charged for either receipt of the data from the second transceiver or for its use for commercial purposes. Any rewards or charging may be arranged electronically. The methods may be enabled by distributed or web-based computer network systems in which any collected data is accessible through a hub on the network. The hub may incorporate various security features to ensure patient confidentiality and to allow selective access to information collected dependent upon level of authorisation. The level of user authorisation may be allocated primarily to safeguard patient confidentiality. Beyond this the level of user authorisation may also be allocated on commercial terms with for example broader access to the database being authorised in return for larger commercial payments.

Suitably, the first and second transceiver each comprise an antenna or equivalent for transmitting or receiving data and connecting thereto a memory. The memory will typically comprise an integrated circuit chip. Either transceiver may be configured to have a memory structure which allows for large amounts of information to be stored thereon. The memory structure can be arranged such that parts of the memory are read-only, being programmed during/after manufacture, other parts are read/write and further parts are password protectable. Initial transfer of information (e.g. on manufacture or one dispensing) to or from any transceiver can be arranged to be readily achievable by the use of a reader which is remote from the medical dispenser, thereby minimising the need for direct product handling. In further aspects, the reader can be arranged to simultaneously read or write to the memory of multiple transceivers on multiple medicament dispensers.

A suitable power source such as a battery, clockwork energy store, solar cell, fuel cell or kinetics-driven cell will be provided as required to any electronic component herein. The power source may be arranged to be rechargeable or reloadable.

Suitably, data is transferable in two-way fashion between the first and second transceiver without the need for direct physical contact therebetween. Preferably, data is transferable wirelessly between the first and second transceiver.

Suitably, the first transceiver is an active transceiver and the second transceiver is a passive transceiver. The term active is used to mean directly powered and the term passive is used to mean indirectly powered.

Suitably, the second transceiver comprises a label or tag comprising an antenna for transmitting or receiving energy; and an integrated circuit chip connecting with said antenna, and the first transceiver comprises a reader for said label or tag. In this case the label or tag is a passive transceiver and the reader is an active transceiver. Preferably, the reader will not need to be in direct contact with the tag or label to enable the tag or label to be read.

The tag may be used in combination and/or integrated with other traditional product labelling methods including visual text, machine-readable text, bar codes and dot codes.

Suitably, the integrated circuit chip has a read only memory area, a write only memory area, a read/write memory area or combinations thereof.

Suitably, the integrated circuit chip has a one-time programmable memory area. More preferably, the one-time programmable memory area contains a unique serial number.

Suitably, the integrated circuit chip has a preset memory area containing a factory preset, non-changeable, unique data item. The preset memory item is most preferably in encrypted form.

Suitably, the integrated circuit chip has plural memory areas thereon. Suitably, any memory area is password protected.

Suitably, any memory area contains data in encrypted form. Electronic methods of checking identity, error detection and data transfer may also be employed.

In one aspect, the integrated circuit has plural memory areas thereon including a read only memory area containing a unique serial number, which may for example be embedded at the time of manufacture; a read/write memory area which can be made read only once information has been written thereto; and a password protected memory area containing data in encrypted form which data may be of anti-counterfeiting utility.

Suitably, the tag is on a carrier and the carrier is mountable on the body or housing of the medicament dispenser or the medicament container. In one aspect, the carrier is a flexible label. In another aspect, the carrier is a rigid disc. In a further aspect, the carrier is a rectangular block. In a further aspect, the carrier is a collar ring suitable for mounting to the neck of an aerosol container. Other shapes of carrier are also envisaged.

Suitably, the carrier is mouldable or weldable to the medicament container or housing. Suitably, the carrier encases the tag. More preferably, the carrier forms a hermetic seal for the tag.

In one aspect, the carrier comprises an insulating material such as a glass material or, a paper material or an organic polymeric material such as polypropylene. Alternatively, the carrier comprises a ferrite material.

The energy may be in any suitable form including ultrasonic, infrared, radiofrequency, magnetic, optical and laser form. Any suitable channels may be used to channel the energy including fibre optic channels.

In one aspect, the second transceiver comprises a radiofrequency identifier comprising an antenna for transmitting or receiving radiofrequency energy; and an integrated circuit chip connecting with said antenna, and the first transceiver comprises a reader for said radiofrequency identifier. In this case the radiofrequency identifier is a passive transceiver and the reader is an active transceiver. An advantage of radiofrequency identifier technology is that the reader need not be in direct contact with the radiofrequency identifier tag or label to be read.

The radiofrequency identifier can be any known radiofrequency identifier. Such identifiers are sometimes known as radiofrequency transponders or radiofrequency identification (RFID) tags or labels. Suitable radiofrequency identifiers include those sold by Phillips Semiconductors of the Netherlands under the trade marks Hitag and Icode, those sold by Amtech Systems Corporation of the United States of America under the trade mark Intellitag, and those sold by Texas Instruments of the United States of America under the trade mark Tagit.

Suitably, the antenna of the RFID tag is capable of transmitting or receiving radiofrequency energy having a frequency of from 100 KHz to 2.5 GHz. Preferred operating frequencies are selected from 125 KHz, 13.56 MHz and 2.4 GHz.

In one aspect, the second transceiver comprises a magnetic label or tag comprising an antenna for transmitting or receiving magnetic field energy; and an integrated circuit chip connecting with said antenna, and the first transceiver comprises a reader for said magnetic label or tag. In this case the magnetic label or tag is a passive transceiver and the reader is an active transceiver.

A suitable magnetic label or tag comprises plural magnetic elements in mutual association whereby the magnetic elements move relative to each other in response to an interrogating magnetic field. A magnetic label or tag of this type is described in U.S. Pat. No. 4,940,966. Another suitable magnetic label or tag comprises a magnetorestrictive element which is readable by application of an interrogating alternating magnetic field in the presence of a magnetic bias field which results in resonance of the magnetorestrictive elements at different predetermined frequencies. A magnetic label of this type is described in PCT Patent Application No. WO92/12402. Another suitable magnetic label or tag comprising plural discrete magnetically active regions in a linear array is described in PCT Patent Application No. WO96/31790. Suitable magnetic labels and tags include those making use of Programmable Magnetic Resonance (PMR) (trade name) technology.

In another aspect, the second transceiver comprises a microelectronic memory chip and the first transceiver comprises a reader for said microelectronic memory chip. The microelectronic memory chip may comprise an Electrically Erasable Programmable Read Only Memory (EEPROM) chip or a SIM card-type memory chip. In this case the microelectronic memory chip is a passive transceiver and the reader is an active transceiver.

Any transceiver herein, particularly a passive transceiver may be mounted on or encased within any suitable inert carrier. The carrier may comprise a flexible sheet which may in embodiments be capable of receiving printed text thereon.

In one aspect, the first transceiver is integral with the body such that a single unit is comprised. The first transceiver may for example be encased within or moulded to the body.

In another aspect, the first transceiver forms part of a base unit which is reversibly associable with the body. The base unit may for example, form a module receivable by the body such as a snap-in module.

Suitably, the medicament dispenser additionally comprises a communicator for wireless communication with a network computer system to enable transfer of data between the network computer system and the electronic data management system. Dispensers employing such communicators are described in pending PCT Applications No.s PCT/EP00/09291 (PG3786), PCT/EP00/09293 (PG4029) and PCT/EP00/09292 (PG4159). Preferably, the communicator enables two-way transfer of data between the network computer system and the electronic data management system.

Suitably, the data is communicable between the network computer system and the electronic data management system in encrypted form. All suitable methods of encryption or partial encryption are envisaged. Password protection may also be employed. Suitably, the communicator employs radiofrequency or optical signals.

In one aspect, the communicator communicates via a gateway to the network computer system. In another aspect, the communicator includes a network server (e.g. a web server) such that it may directly communicate with the network.

In a further aspect, the communicator communicates with the gateway via a second communications device. Preferably, the second communications device is a telecommunications device, more preferably a cellular phone or pager. Preferably, the communicator communicates with the second communications device using spread spectrum radiofrequency signals. A suitable spread spectrum protocol is the Bluetooth (trade mark) standard which employs rapid (e.g. 1600 times a second) hopping between plural frequencies (e.g. 79 different frequencies). The protocol may further employ multiple sending of data bits (e.g. sending in triplicate) to reduce interference.

In one aspect, the network computer system comprises a public access network computer system. The Internet is one suitable example of a public access network computer system, wherein the point of access thereto can be any suitable entrypoint including an entrypoint managed by an Internet service provider. The public access network computer system may also form part of a telecommunications system, which may itself be either a traditional copper wire system, a cellular system or an optical network.

In another aspect, the network computer system comprises a private access network computer system. The private access network system may for example, comprise an Intranet or Extranet which may for example, be maintained by a health service provider or medicament manufacturer. The network may for example include password protection; a firewall; and suitable encryption means.

Preferably, the communicator enables communication with a user-specific network address in the network computer system.

The user-specific network address may be selected from the group consisting of a web-site address, an e-mail address and a file transfer protocol address. Preferably, the user-specific network address is accessible to a remote information source such that information from said remote information source can be made available thereto. More preferably, information from the user-specific network address can be made available to the remote information source.

In one aspect, the remote information source is a medicament prescriber, for example a doctor's practice. Information transferred from the medicament prescriber may thus, comprise changes to prescription details, automatic prescription updates or training information. Information transferred to the medicament prescriber may comprise compliance information, that is to say information relating to the patient's compliance with a set prescribing programme. Patient performance information relating for example, to patient-collected diagnostic data may also be transferred to the medicament prescriber. Where the dispenser is an inhaler for dispensing medicament for the relief of respiratory disorders examples of such diagnostic data would include breath cycle data or peak flow data.

In another aspect, the remote information source is a pharmacy. Information transferred from the pharmacy may thus, comprise information relating to the medicament product. Information sent to the pharmacy may thus include prescription requests which have been remotely pre-authorised by the medicament prescriber.

In a further aspect, the remote information source is an emergency assistance provider, for example a hospital accident and emergency service or an emergency helpline or switchboard. The information may thus, comprise a distress or emergency assist signal which requests emergency assistance.

In a further aspect, the remote information source is a manufacturer of medicament or medicament delivery systems. Information transferred to the system may thus, comprise product update information. The system may also be configured to feed information back to the manufacturer relating to system performance.

In a further aspect, the remote information source is a research establishment. In a clinical trial situation, information may thus be transferred relating to the trial protocol and information relating to patient compliance fed back to the research establishment.

In a further aspect, the remote information source is an environmental monitoring station. Information relating to weather, pollen counts and pollution levels may thus be made accessible to the system.

In a further aspect, the remote information source is a computer software download site from which software may be downloaded for use in the electronic data management system. Embodiments are envisaged in which such software downloads are employed to upgrade or modify any existing software employed by the electronic data management system.

Suitably, the medicament dispenser additionally comprises a geographic positioning system such as a global positioning system or a system which relies on the use of multiple communications signals and a triangulation algorithm.

According to another aspect of the present invention there is provided an actuator for a medicament container having a dispensing mechanism comprising a container seat for receipt of the medicament container; a dispenser seat for receipt of the dispensing mechanism; and a coupling between said container seat and said dispenser seat capable on deformation of moving the container seat relative to the dispenser seat to actuate the dispensing mechanism. The coupling is reversibly deformable in response to the application of non-mechanical energy thereto.

According to a further aspect of the present invention there is provided an actuator for a medicament container having a dispensing mechanism comprising a housing; within said housing, a container seat for receipt of the medicament container; on the housing or connecting therewith, an anchor station; and a coupling between said container seat and said anchor station capable on deformation of moving the container seat relative to the anchor station to actuate the dispensing mechanism, wherein the coupling is reversibly deformable in response to the application of non-mechanical energy thereto.

According to a further aspect of the present invention there is provided an actuator for a medicament dispenser having a medicament container and separately an aerosol container having a dispensing mechanism comprising a housing, shaped for receipt of said medicament container for containing medicament for release; within said housing, a container seat for receipt of said aerosol container having a dispensing mechanism; an anchor station on the housing or connecting therewith; and a coupling between said container seat and said anchor station capable on deformation of moving the container seat relative to the anchor station to actuate the dispensing mechanism to energise released medicament, wherein the coupling is reversibly deformable in response to the application of non-mechanical energy thereto.

According to a further aspect of the present invention there is provided an actuator for a medicament dispenser having a medicament container and separately an aerosol container having a dispensing mechanism comprising a housing, shaped for receipt of said medicament container for containing medicament for release; an aerosol container having a dispensing mechanism; a container seat for receipt of said aerosol container having a dispensing mechanism; a dispenser seat for receipt of the dispensing mechanism; and a coupling between said container seat and said dispenser seat capable on deformation of moving the container seat relative to the dispenser seat to actuate the dispensing mechanism to energise released medicament, wherein the coupling is reversibly deformable in response to the application of non-mechanical energy thereto.

The actuator herein may be configured to include, as relevant, any of the above described features of the medicament dispenser. In particular, the actuator may be configured to include an electronic data management system comprising control means for the actuation of the coupling.

Preferably, the non-mechanical energy comprises electric current flow through the coupling.

In one embodiment, the coupling comprises one or more wires which contract in response to application of non-mechanical energy thereto. More preferably, the one or more wires comprise an alloy which undergoes a phase transition on heating, for example in response to flow of electrical current therethrough. The alloy is for example, a nickel-titanium alloy.

In another embodiment, the one or more wires comprise an alloy which undergoes a phase transition on application of a magnetic field thereto (magnetic shape memory alloys).

Suitably, the actuator additionally comprises an electronic control system for controlling the supply of non-mechanical energy to the coupling. Suitably, the electronic control system is capable of providing pulses of non-mechanical energy to the coupling.

Suitably, the electronic control system is capable of receiving inputs from electronic sensors locatable on the dispenser. Suitably, the actuator additionally comprises an electronic sensor selected from the group consisting of a breath sensor, a shake sensor, a temperature sensor, an infrared sensor and a patient ID sensor.

According to a further aspect of the present invention there is provided a laboratory test apparatus comprising at least one actuator as described above and a mounting (e.g. a bench mounting) for the at least one actuator. The laboratory test apparatus is designed for use in testing the performance of the medicament dispenser in a laboratory environment. Often, plural actuators will be mounted on a single mounting to enable simultaneous testing thereof. The laboratory test apparatus will typically be connected to various sensors and recording devices for monitoring aspects of the performance of the medicament dispenser.

According to a further aspect of the present invention there is provided a kit of parts comprising a medicament dispenser as described above in the form of a cartridge; and a housing shaped for receipt of said cartridge.

According to a further aspect of the present invention there is provided a kit of parts comprising an actuator as described above and, receivable by said actuator, a medicament container having a dispensing mechanism.

In a preferred commercial embodiment herein, the actuator is arranged for receipt of a refill cartridge. Typically, the actuator is in the form of a relatively complex device, including for example an electronic data management system and the cartridge is in the form of a medicament refill therefor.

In another aspect the cartridge comprises a medicament dispenser having a voltaic cell as an electrical energy source and the housing is provided with a mouthpiece or nozzle for patient inhalation therethrough and electronic information display apparatus for displaying information to the patient.

The invention will now be described further with reference to the accompanying drawings in which:

FIG. 1b is a side view of the medicament dispenser of FIG. 1a;

FIG. 7b is a sectional view of the laboratory test apparatus of FIG. 7a;

FIG. 9a shows an active DPI type medicament dispenser according to another aspect of the invention in a rest position; and FIG. 9b shows the medicament dispenser of FIG. 9a in a 'ready to fire' position.

Figure 1C:
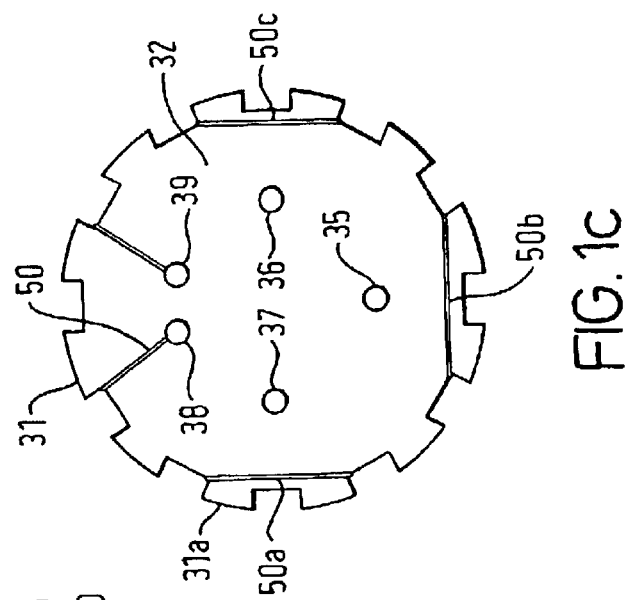
FIG. 1c is sectional top view of part of the container seat of the medicament dispenser of FIGS. 1a and 1b.
Figure 1B:
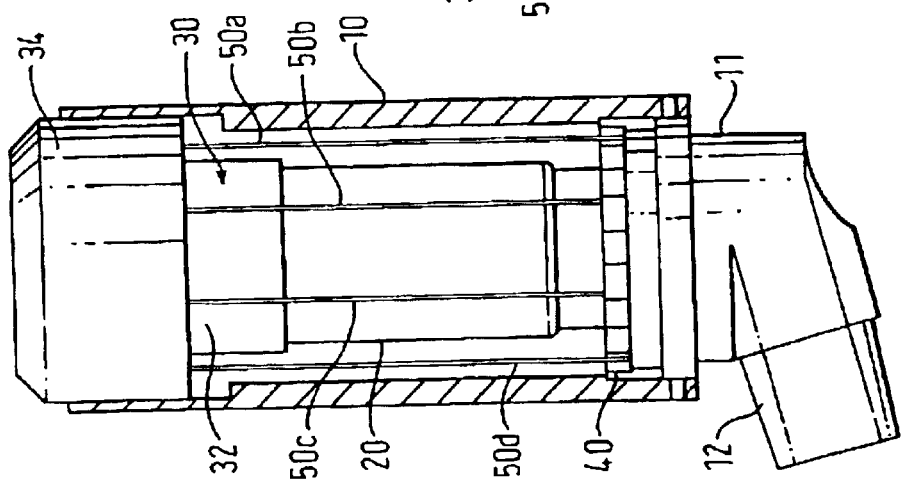
Figure 1A:
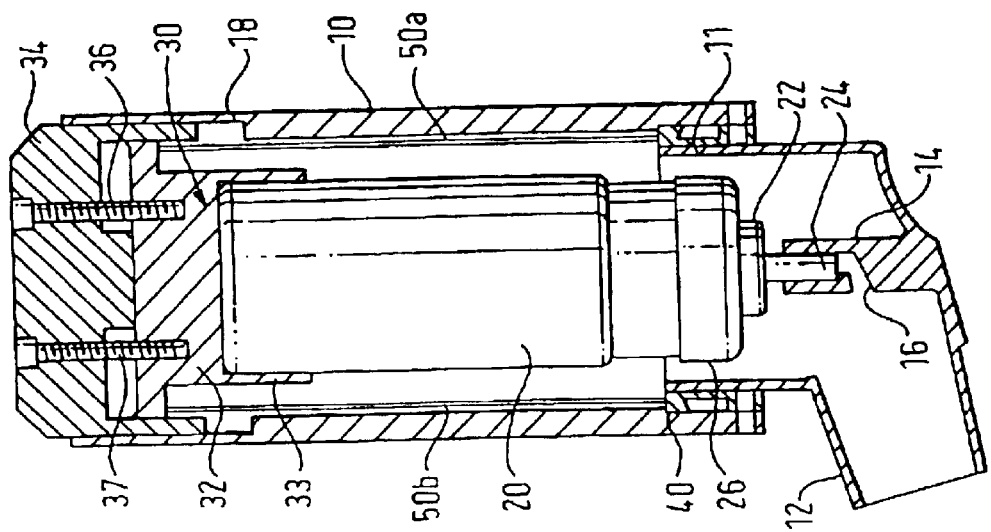
FIG. 1a is a sectional side view of a first medicament dispenser in accord with the present invention.

FIGS. 1a and 1b show a metered dose inhaler for the delivery of medicament for inhalation by a patient. The inhaler comprises a tubular housing 10 in which an aerosol container 20 is located. A dispensing outlet 12 leads laterally from the closed end of the housing 10. In the embodiment illustrated, the outlet 12 is in the form of a mouthpiece intended for insertion into the mouth of the patient but it may, if desired, be designed as a nozzle for insertion into the patient's nostril.

The aerosol container 20 has a valve dispensing mechanism 22 in the form of a slide valve. Valve stem 24 connects with a support 14. The support 14 is provided with an outlet passage 16 enabling dispensed dose to pass through to the dispensing outlet 12. It will be appreciated that dispensing of the dose requires the aerosol container 20 to be depressed to actuate the slide valve dispensing mechanism 22 and dispense medicament into the outlet 12 from which it can be inhaled by a patient.

It may be seen that the upper part of the aerosol container 20 is received by container seat 30. The container seat 30 is slidably movable within the housing along track 18 cut it into the wall of the housing 10. The container seat 30 comprises a first electrically conducting portion 32 having receiving side walls 33 to receive the aerosol container 20 and a second portion 34 which forms a manual actuation button for use as a manual override. The first portion 32 is fixed to the second portion 34 via screw connectors 36, 37. It may also be seen that the neck 26 of the valve 22 is received by electrically conducting ring 40 which fits around the neck 26 of the valve 22. The ring 40 is itself fixed to the lower part 11 of the housing 10. Plural lengths of shape memory alloy wire 50a, 50b, 50c, 50d connect the first portion 32 of the container seat 30 to the conducting ring 40. As will become apparent by inspection of FIG. 1c, the plural lengths of wire 50a, 50b, 50c, 50d in fact, comprise a single wire 50 wrapped a number of times around the container seat 30 and ring 40. The wire 50 comprises a nickel-titanium alloy which contracts in response to the flow of electrical current therethrough. It may thus, be appreciated that when electrical current is passed through the plural lengths of wire 50a, 50b, 50c, 50d the container seat 30 and ring 40 will be drawn towards each other as the wire 50 contracts. Actuation of the valve dispensing mechanism 22 and dispensing of medicament dose will thereby result.

In the event of failure of electrical current flow it may be appreciated that the manual actuation button 34 may be manually pushed downwards to actuate the valve dispensing mechanism 22.

FIG. 1c shows a top view of the first portion 32 of the container seat 30. It may be seen that the first portion 32 is provided with crenellations 31, 31a around its circumference. First and second points of wire attachment 38, 39 are provided such that a first end of shape memory alloy wire 50 is fixed to the first point of attachment 38. The wire 50 is then wrapped around first crenellations 31 and trailed down to the valve seat 40 with which it connects before leading up to second crenellations 31 around which it is wrapped and so on until multiple loops of wire 50a, 50b, 50c connect the ring 40 to the container seat 30. The end of the wire 50 is finally pulled taught and secured to end point of attachment 39. In alternative embodiments, a tensioning feature such as a screw tension mechanism may be included for use in tensioning the wire. Screw connector holes 36, 37 are provided to enable screw connection to the upper part 34 of the container seat 30. A power connector 35 is provided to enable connection of the first portion 32 and hence, wire 50 to an electrical power source.

Figure 2:
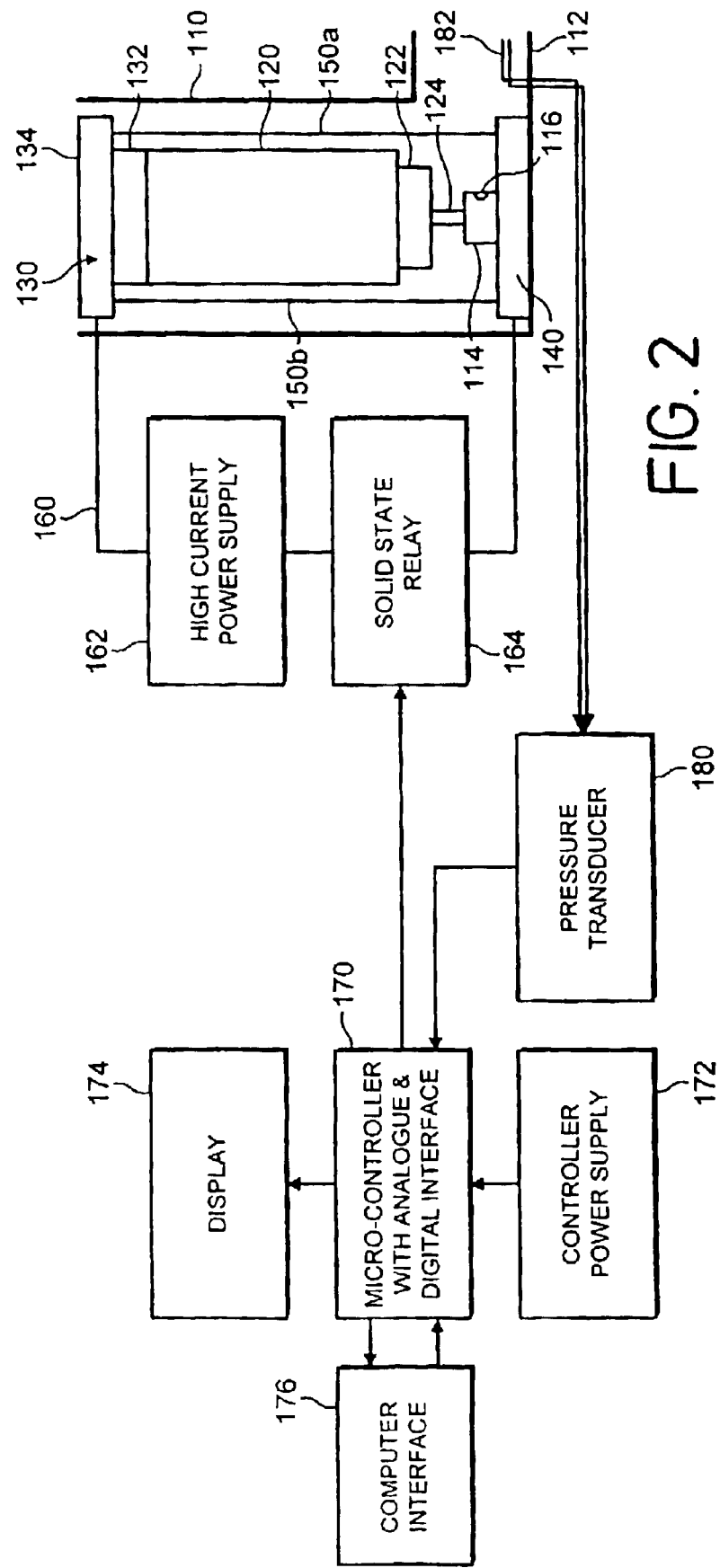
FIG. 2 is a schematic view of a system for dispensing medicament in accord with the present invention.

FIG. 2 shows a schematic representation of a breath-operable medicament dispensing system herein. The system comprises a metered dose inhaler similar to that shown in more detail in FIGS. 1a, 1b and 1c comprising tubular housing 110 having a dispensing outlet 112 in the form of a mouthpiece. Within the housing 110 sits aerosol container 120 which has a valve dispensing mechanism 122 in the form of a slide valve. Valve stem 124 is supported by valve support 114. Outlet passage 116 is provided in the support 114 to enable passage of dispensed dose to the dispensing outlet 112.

It may be seen that the upper part of the aerosol container 120 abuts container seat 130. The container seat 130 comprises an insulating portion 132 which directly contacts the aerosol container 120 and an upper conducting portion 134 (e.g. comprised of aluminum). It may also be seen that the valve support 114 connects with conducting valve seat 140. Plural shape memory alloy wires 150a, 150b connect the conducting portion 134 of the container seat 130 to the conducting valve seat 140. The plural wires 150a, 150b comprise a nickel-titanium alloy which contracts in response to electrical current flow therethrough. It may thus, be appreciated that on passage of electrical current through the plural wires 150a, 150b the container seat 130 and valve seat 140 will be drawn towards each other as the wires 150a, 150b contract. Actuation of the valve dispensing mechanism 122 and dispensing of medicament dose will thereby result.

Control of electrical current flow to the container seat 130, valve seat 140 and wires 150a, 150b is achievable using the illustrated circuitry. Container seat 130 and valve seat 140 connect to actuation circuit 160 which includes a high current power supply 162 (e.g. a voltaic cell or battery of voltaic cells) and a switch 164 in the form of a solid state relay. The solid state relay 164 itself connects with control circuitry including a micro-controller 170 having an independent power supply 172. The micro-controller 170 itself connects with pressure transducer 180 which has an input in the form of a pressure tube 182 located within the dispensing outlet 112 of the inhaler housing 110.

It may be appreciated that current flow to the container seat 130, valve seat 140 and wires 150a, 150b, and hence actuation of the valve dispensing mechanism may be achievable as follows. The patient inhales through the mouthpiece 112 resulting in a change in pressure within the housing 110 and pressure tube 182. The change in pressure is detected by the pressure transducer 180 which sends a signal to the micro-controller 170. The micro-controller 170, in turn sends a switching signal to the solid state relay 164 which results in closing of the actuation circuit and electrical current flow therethrough. The resulting contraction of the shape memory alloy wires 150a, 150b causes actuation of the valve dispensing mechanism 122 and hence, dispensing of medicament to the inhaling patient.

It may also be seen in FIG. 2 that the micro-controller 170 is connected to a display 174 for display of information to the patient and also with a computer interface 176 for exchange of data therewith. All circuitry and components thereof including the power supplies 162, 172 and display 174 may be arranged to be present on the housing 110 such that the system is in the form of a discrete, hand-held device.

Figure 3:
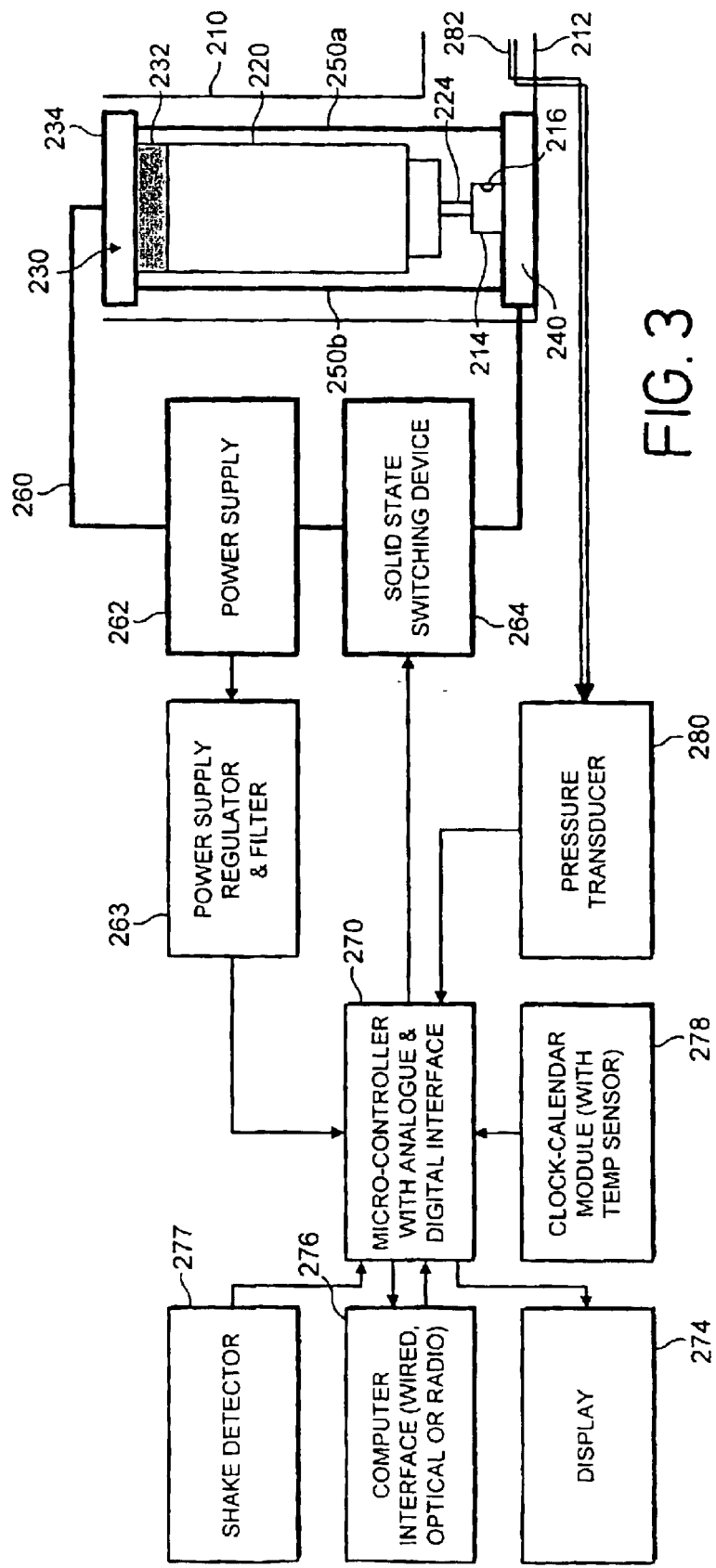
FIG. 3 is a schematic view of a second system for dispensing medicament in accord with the present invention.

FIG. 3 shows a schematic representation of a breath-operable medicament dispensing system herein. The system comprises a metered dose inhaler similar to that shown in more detail in FIGS. 1a, 1b and 1c comprising tubular housing 210 having a dispensing outlet 212 in the form of a mouthpiece. Within the housing 210 sits aerosol container 220 which has a valve dispensing mechanism 222 in the form of a slide valve. Valve stem 224 is supported by valve support 214. Outlet passage 216 is provided in the support 214 to enable passage of dispensed dose to the dispensing outlet 212.

It may be seen that the upper part of the aerosol container 220 abuts container seat 230. The container seat 230 comprises an insulating portion 232 which directly contacts the aerosol container 220 and an upper conducting portion 234 (e.g. comprised of aluminum). It may also be seen that the valve support 214 connects with conducting valve seat 240. Plural shape memory alloy wires 250a, 250b connect the conducting portion 234 of the container seat 230 to the conducting valve seat 240. The plural wires 250a, 250b comprise a nickel-titanium alloy which contracts in response to electrical current flow therethrough. It may thus, be appreciated that on passage of electrical current through the plural wires 250a, 250b the container seat 230 and valve seat 240 will be drawn towards each other as the wires 250a, 250b contract. Actuation of the valve dispensing mechanism 222 and dispensing of medicament dose will thereby result.

Control of electrical current flow to the container seat 230, valve seat 240 and wires 250a, 250b is achievable using the illustrated circuitry. Container seat 230 and valve seat 240 connect to actuation circuit 260 which includes a power supply 262 (e.g. a voltaic cell or battery of voltaic cells) and a switch 264 in the form of a solid state switching device. The switch 264 itself connects to control circuitry including micro-controller 270 which has an analogue and digital interface. The power supply for the control circuitry is taken from the power supply 262 for the wires 250a, 250b after suitable regulation and filtering 263. The micro-controller 270 itself connects with pressure transducer 280 which has an input in the form of a pressure tube 282 located within the dispensing outlet 212 of the inhaler housing 210.

It may be appreciated that current flow to the container seat 230, valve seat 240 and wires 250a, 250b, and hence actuation of the valve dispensing mechanism 222 may be achievable as follows. The patient inhales through the mouthpiece 212 resulting in a change in pressure within the housing 210 and pressure tube 282. The change in pressure is detected by the pressure transducer 280 which sends a signal to the micro-controller 270. The micro-controller 270, in turn sends a switching signal to the solid state switching device 264 which results in closing of the actuation circuit and electrical current flow therethrough. The resulting contraction of the shape memory alloy wires 250a, 250b causes actuation of the valve dispensing mechanism 222 and hence, dispensing of medicament to the inhaling patient.

It may also be seen in FIG. 3 that the micro-controller 270 is connected to a display 274 for display of information to the patient and also with a computer interface 276 for exchange of data therewith. Communication with the computer interface 276 may be via a wired, optical or radio communications link. The micro-controller 270 is also connected to shake detector 277 for use in detecting whether the container 220 is shaken prior to actuation of the valve dispensing mechanism 222 and to a clock-calendar module 278 including a temperature sensor. All circuitry and components thereof including the power suppy 262, display 274, shake detector 277, computer interface 276 and clock-calendar module 278 may be arranged to be present on the housing 210 such that the system is in the form of a discrete, hand-held device.

Figure 4:
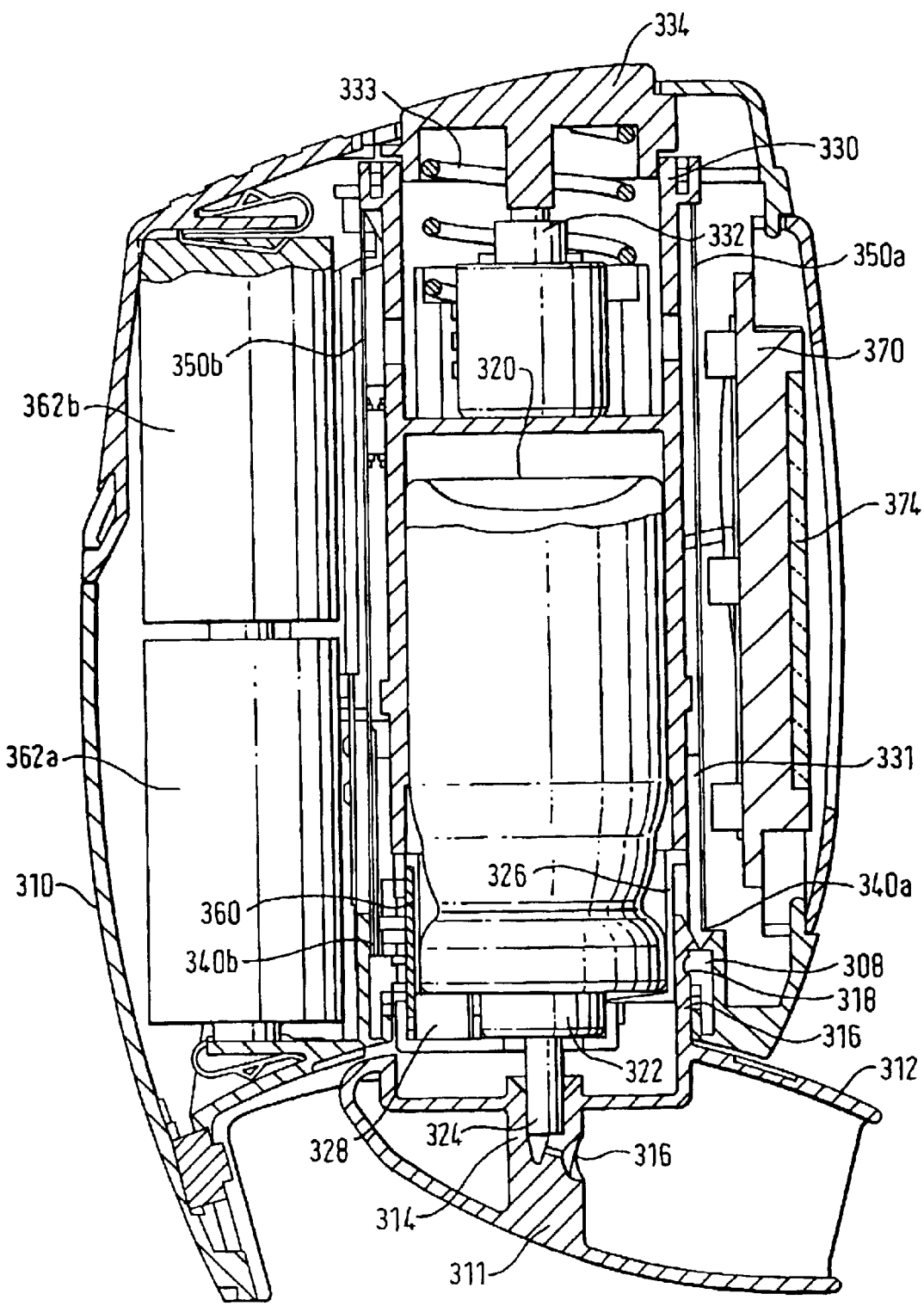
FIG. 4 is a sectional view of a third system for dispensing medicament in accord with the present invention.

FIG. 4 shows a metered dose inhaler for the delivery of medicament for inhalation by a patient. The inhaler comprises a housing 310 in which an aerosol container 320 is located. An endpiece 311 in the form of a mouthpiece 312 is provided to the aerosol container 320.

The aerosol container 320 has a valve dispensing mechanism 322 in the form of a slide valve. Valve stem 324 connects with a stem support 314 which forms part of the endpiece 311. The support 314 is provided with an outlet passage 316 enabling dispensed dose to pass through to the mouthpiece outlet 312. It will be appreciated that dispensing of the dose requires the aerosol container 320 to be depressed to actuate the slide valve dispensing mechanism 322 and dispense medicament into the outlet 312 from which it can be inhaled by a patient.

The endpiece 311 has a tubular neck portion 316 for receipt of a collar 326 which itself engages the neck of the aerosol container 320. The tubular portion 316 is shaped such that collar 326 and so-engaged aerosol container are sufficiently movable in a sliding fashion therein to enable actuation of the slide valve mechanism 322. The aerosol container 320, collar 326 and end-piece 311 together form a discrete unit which is reversibly removable from the housing 310 when the end-piece 311 is in certain orientations. The drawing shows the endpiece in the 'endpiece secured orientation' in which retaining lip 308 makes snap-fit engagement with groove 318 provided in the tubular portion 316 of the endpiece. A perpendicularly opposing point (i.e. 90° rotation therefrom) on the tubular portion 316 has no similar groove portion, such that when the endpiece 311 is rotated through 90° to the 'endpiece unsecured orientation' the endpiece 311, collar 326 and aerosol container may be removed from the housing 310.

The collar 326 is provided with an electronic memory chip 328 which is capable of receiving data inputs and providing data outputs. The memory chip 328 connects via contact 360 to electronic circuitry (not visible) and power supply in the form of two lithium batteries 362a and 362b. The electronic circuitry further connects to electronic control system 370 which is capable of communication with the memory chip 328 and with various sensors on the device (for simplicity, not shown) and of providing visual output via display 374 to the patient. Further aspects of a suitable electronic control system are described in FIG. 5.

It may be seen that the upper part of the aerosol container 320 is received by container seat 330. The container seat 330 is slidably movable within the housing along track 331 formed within the housing 310. The container seat 330 also comprises a spring actuator return 333 and actuator button 334 for use as a manual override. Plural lengths of shape memory alloy wire 350a, 350b (only two wires shown for simplicity) connect the container seat 330 to anchor positions 340a, 340b in the lower part of the housing. The wires 350a, 350b comprise a nickel-titanium alloy which contracts in response to the heating effect of the flow of electrical current therethrough. It may thus, be appreciated that when electrical current is passed through the plural lengths of wire 350a, 350b the container seat 330 will be drawn towards to the anchor positions 340a, 340b as the wires 350a, 350b contract. Actuation of the valve dispensing mechanism 322 and dispensing of medicament dose will thereby result. The flow of electrical current is controlled by the control system 370, which is itself responsive to inputs from various sensors (not shown) such as a sensor which senses the breath of a patient.

In the event of failure of electrical current flow it may be appreciated that the manual actuation button 334 may be manually pushed downwards to actuate the valve dispensing mechanism 322. The manuation actuation step also results in the closing of switch 332 which records that a dose has been fired.

Figure 5:
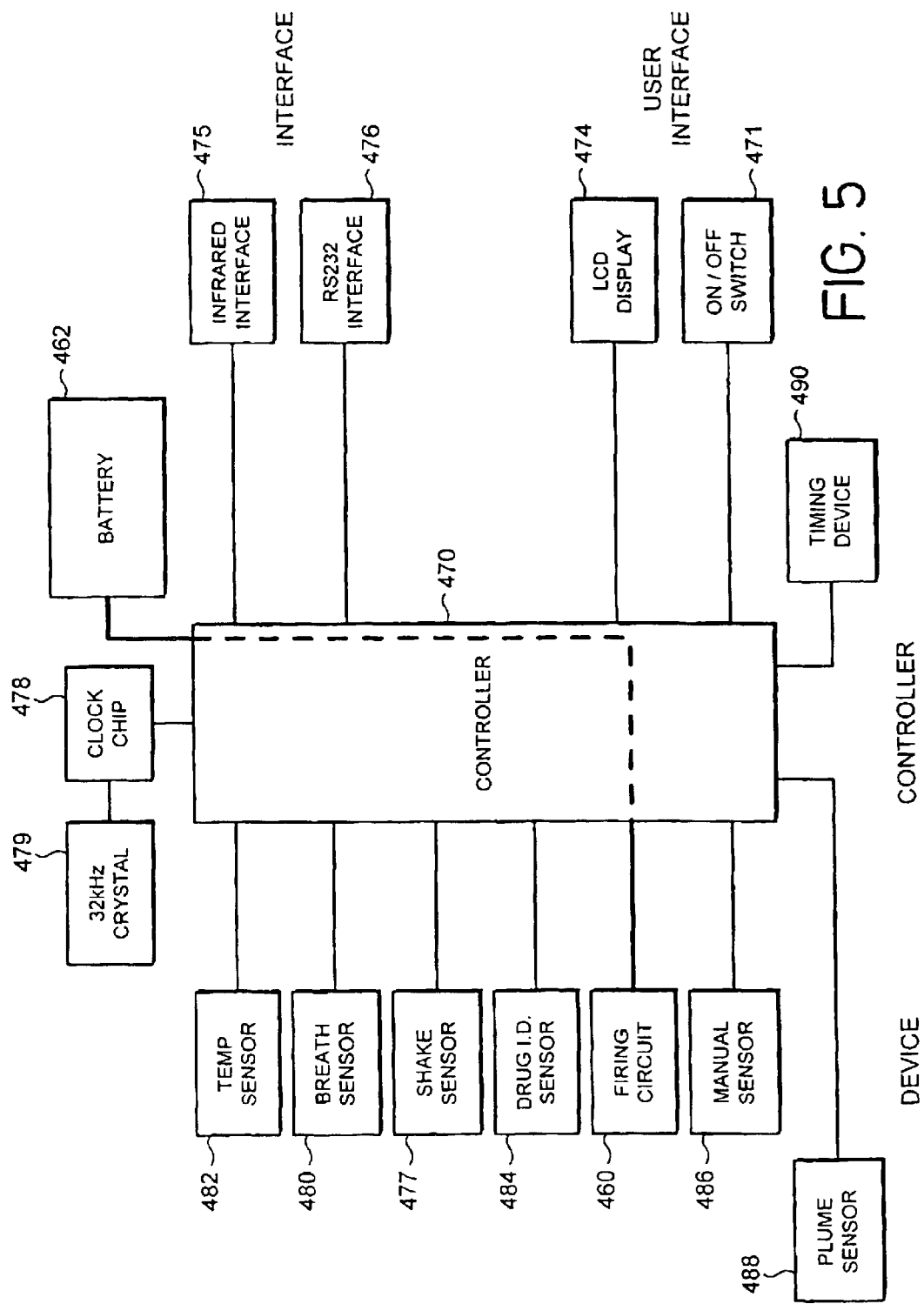
FIG. 5 is a schematic view of an electronic control system for use in accord with medicament dispensers herein.

FIG. 5 shows a schematic representation of electronic components for use in a dispenser herein and an electronic control system therefor. The control system is essentially a more sophisticated version of the system shown in FIGS. 2 and 3 and is suitable, in aspects for use in controlling the device of FIG. 4. Central controller 470 receives inputs and/or transmits outputs to each of the respective components. Key components associated with the central controller are clock chip 478 and 32 KHz crystal 479 and a power supply 462 in the form of a battery. A suitable battery 462 delivers 6 Volts at 1.3 Amps/Hour and is capable of supplying 4.5 Amps. The central controller 470 communicates with various sensors on the device including a temperature sensor 482 for sensing ambient temperature; a breath sensor 480 (e.g. in the form of a pressure transducer) for sensing the breath of a patient; a shake sensor 477 for detecting shaking of the device; a Drug ID sensor 484 for reading information from a transceiver on a medicament container to check drug identity and integrity; a manual sensor 486 (e.g. in the form of a switch) for detecting manual actuation of the device; a plume sensor 488 (e.g. in the form an infra red emitter/detector) for detecting firing from the medicament container.

Figure 6:
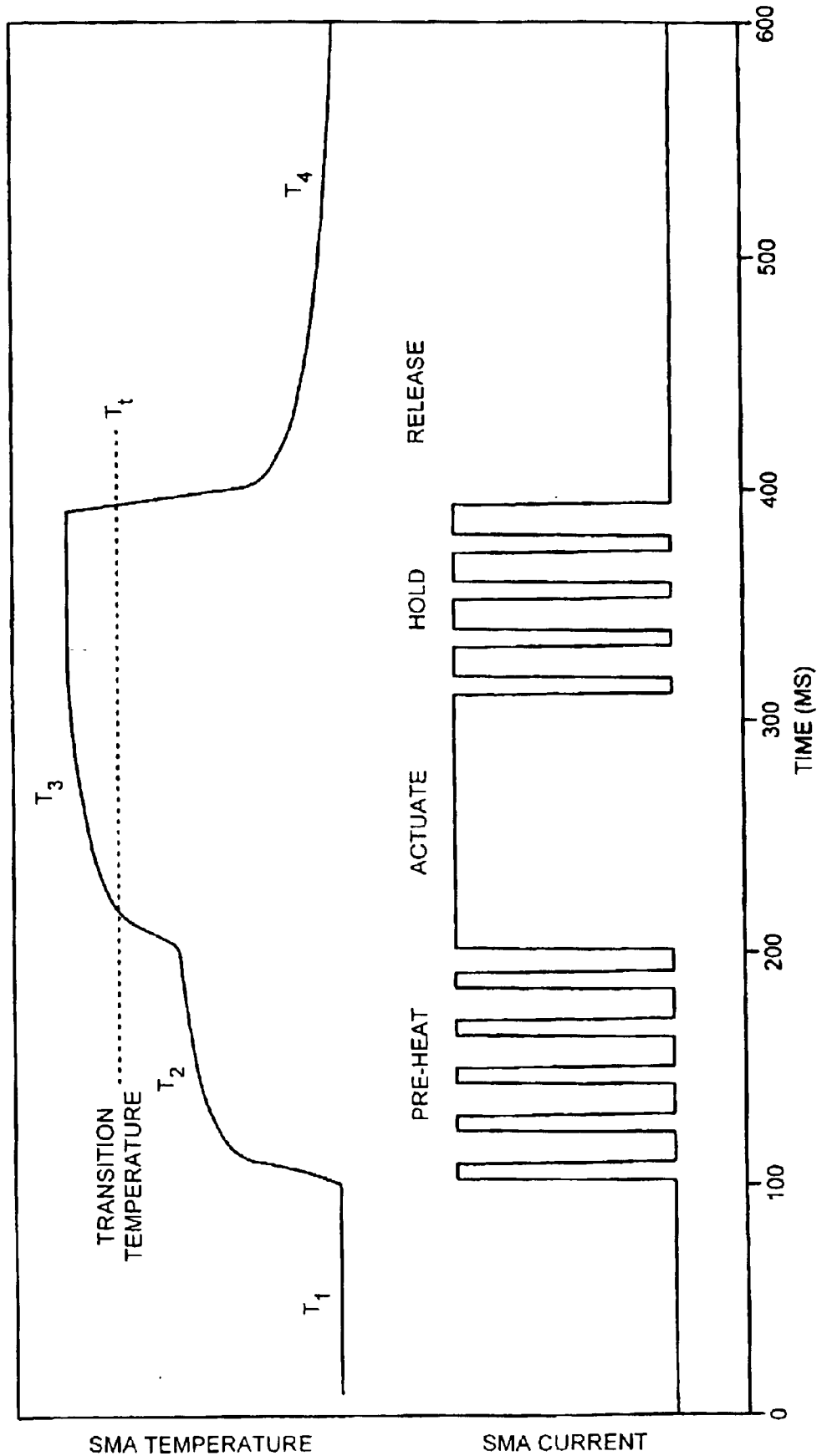
FIG. 6 is a schematic view of a pulse width modulated actuation scheme for use in accord with the present invention.

Firing circuit 460 for delivery of electrical current to heat shape memory alloy wires (not shown) further communicates with the controller 470. System clock 490 (e.g. in the form of a crystal or ceramic resonator) enables control over the supply of electrical current to the firing circuit 460. FIG. 6 shows electrical current and temperature profiles herein, although variations may be employed. User interface features comprising an on/off switch 471 and LCD display 474 also communicate with the central controller 470. External communications interfaces comprising an RS232 interface 476 and infra red interface 475 for data transfer to a docking station or printer are also provided.

It will be appreciated that each of the components of the control system may perform an independent function, or that the action of components may be combined to facilitate the working of the system as a whole. An example of a combination action would be sensing of a patient's inhalation by the breath sensor 480; communication of that breath sensing to the controller 470; communication from the controller 470 to the timing device 490 which controls electrical current flow to the firing circuit 460; the resulting firing of the drug dispenser by; sensing of that firing by the plume sensor 488; and a 'firing complete' message displayed to the patient at the LCD Display 474.

FIG. 6 shows control of the temperature profile of shape memory alloy wires in a firing operation together with an electrical current profile to achieve that temperature control. The upper plot shows temperature of the shape memory alloy (SMA) temperature versus time (in ms). The lower plot shows the associated electrical current profile versus time (in ms). Focusing initially on the upper plot, the temperature of the SMA wires is initially at a rest temperature ($T_1$) which will be largely determined by the ambient environmental temperature. A pre-heating step then raises the temperature of the SMA wires to a temperature ($T_2$) which is just below (e.g. within 5° C.) the phase transition temperature ($T_t$) thereof. On actuation, the temperature is raised to an actuation temperature ($T_3$) which is just above (e.g. within 5° C. of) the phase transition temperature ($T_t$) of the SMA wires causing contraction thereof. The wires are held at this temperature for a holding period. The temperature of the wires is then allowed to cool to below the transition temperature, at which point the wires relax, and ultimately to a rest temperature which is just below (e.g. within 5° C. of) the phase transition temperature ($T_4$). Focusing now on the lower plot, the electrical current profile to achieve the above temperature profile is shown. The electrical current profile is achievable through the use of pulse wave modulation circuitry. Initially, no current is supplied and the wires remain at the rest temperature ($T_1$). In the pre-heating step, pulses of current are supplied to bring the wires to the holding temperature ($T_2$). During actuation, constant current is initially supplied to raise the rise temperature to the actuation temperature ($T_3$). Pulsed current is then supplied to hold the wires at the actuation temperature ($T_3$) until relaxation of the wires is required, at which point the current is switched off.

It will be appreciated that variations of the temperature and electrical current profiles of FIG. 6 may be employed including variation of pre-heating time, actuation time and holding time and release time. In addition, pulse time, repetition rate and amplitude may be varied to give optimal control.

Figure 7A:
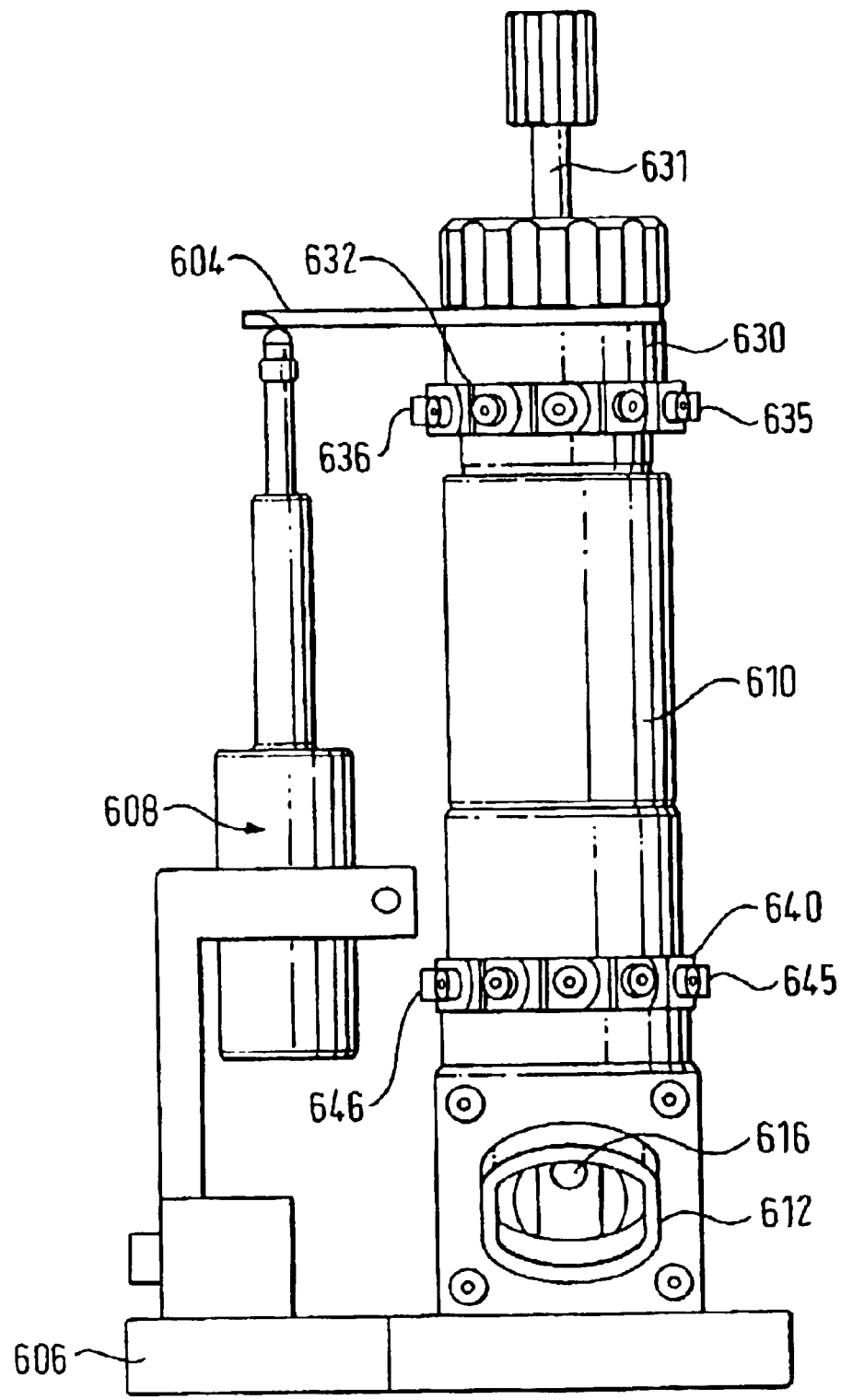
FIG. 7a is a front view of a laboratory test apparatus in accord with the present invention.
Figure 7B:
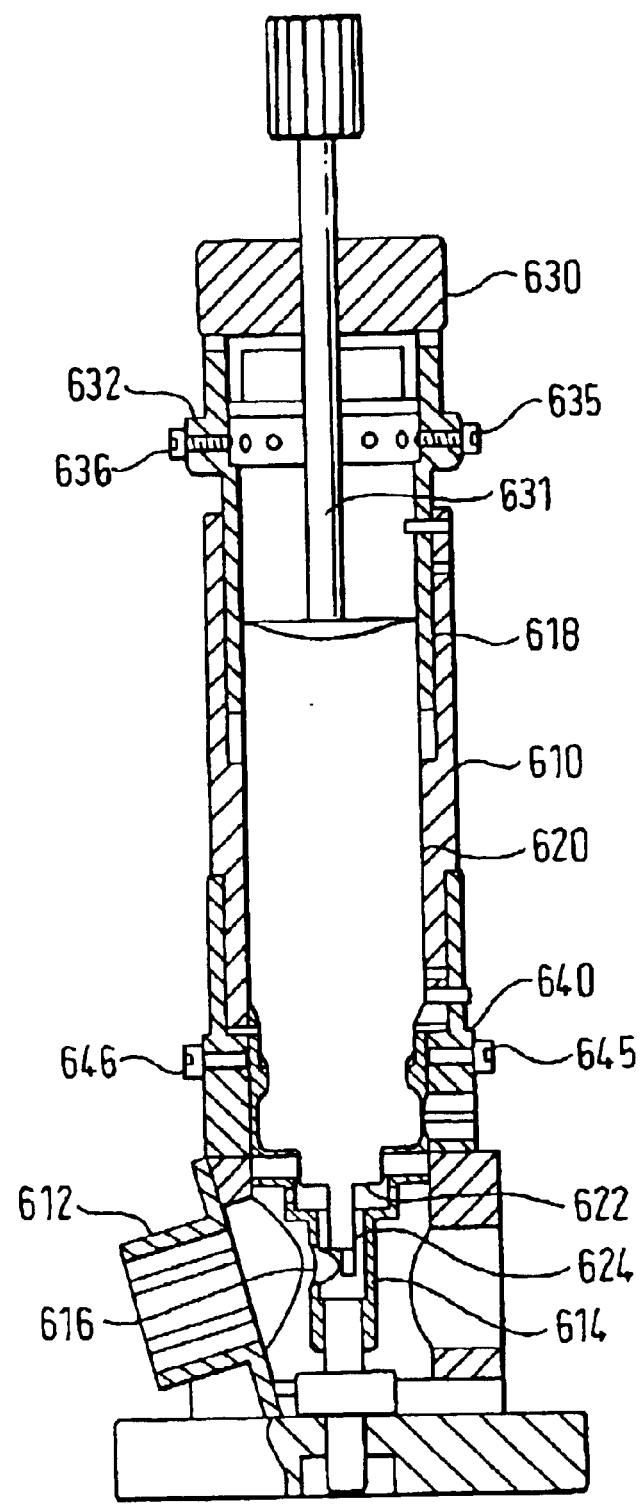

FIGS. 7a and 7b show a laboratory test apparatus for use in the testing of an aerosol container having a valve dispensing mechanism such as may be used in a standard metered dose inhaler. The test apparatus comprises a tubular housing 610 in which an aerosol container 620 is located. The housing is mounted on solid base 606 to enable ready placement on a laboratory bench surface. A dispensing outlet 612 leads laterally from the closed end of the housing 610. In the embodiment illustrated, the outlet 612 has a form similar to that of a mouthpiece as would be found on a standard metered dose inhaler.

The aerosol container 620 has a valve dispensing mechanism 622 in the form of a slide valve. Valve stem 624 connects with a support 614. The support 614 is provided with an outlet passage 616 enabling dispensed dose to pass through to the dispensing outlet 612. It will be appreciated that dispensing of the dose requires the aerosol container 620 to be depressed to actuate the slide valve dispensing mechanism 622 and dispense medicament into the outlet 612.

It may be seen that the upper part of the aerosol container 620 abuts variable tension screw 631 which forms part of container seat 630. The container seat 630 is received within the housing 610 within track 618 cut into the wall of the housing 610. The container seat 630 is provided with a collar 632 comprising a number of wire attachment points 635, 636 (for clarity, not all attachment points are labelled). The lower end of the housing 610 is provided with a similar collar 640 also comprising a number of wire attachment points 645, 646 (again for clarity, not all attachment points are labelled). The collars 632, 640 are arranged to enable the attachment of plural lengths of shape memory alloy wire (not shown) to connect the respective wire attachment points 635, 636 and 645, 646 in a coupling arrangement. In alternative embodiments, the plural lengths of wire may comprise a single wire wrapped a number of times around the respective collars (as in FIG. 1c). The wire comprises a nickel-titanium alloy which contracts in response to the flow of electrical current therethrough. It may thus, be appreciated that when electrical current is passed through the plural lengths of wire the collars 632, 640 and hence the container seat 630 and housing 610 will be drawn towards each other as the wire coupling heats up and contracts. Actuation of the valve dispensing mechanism 622 and dispensing of medicament dose will thereby result.

The container seat 630 is coupled through coupling arm 604 to linear displacement transducer 608 (e.g. a linear variable differential transformer) which detects the displacement of the container 620 on actuation. Various other parts of the laboratory test apparatus may optionally be connected to other sensors for monitoring all aspects of the dispensing process. The sensors may comprise any suitable sensor types including optical, electrical and pressure sensors. The sensors may themselves be connected to various electronic recording and data management systems.

Figure 8C:
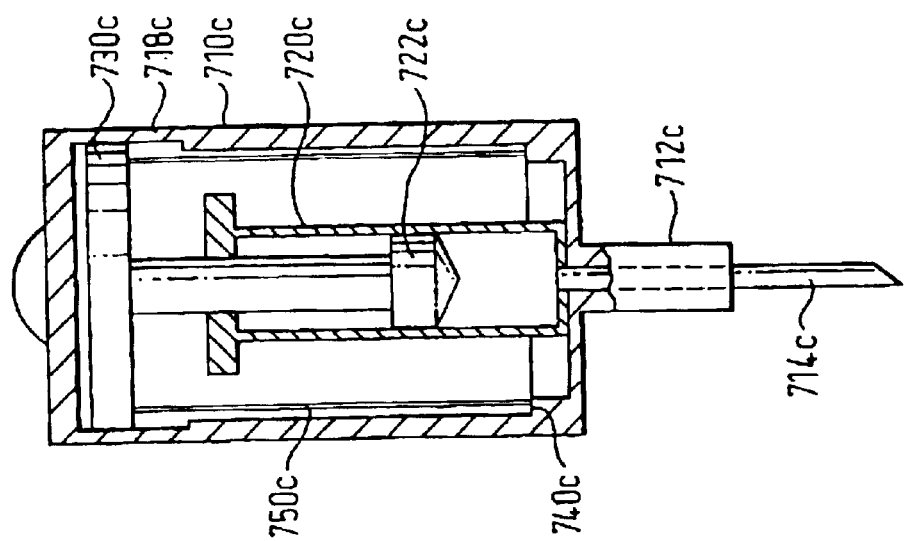
FIGS. 8a–8c are sectional views of a syringe dispenser in accord with the present invention in rest, fire and retract positions respectively.
Figure 8B:
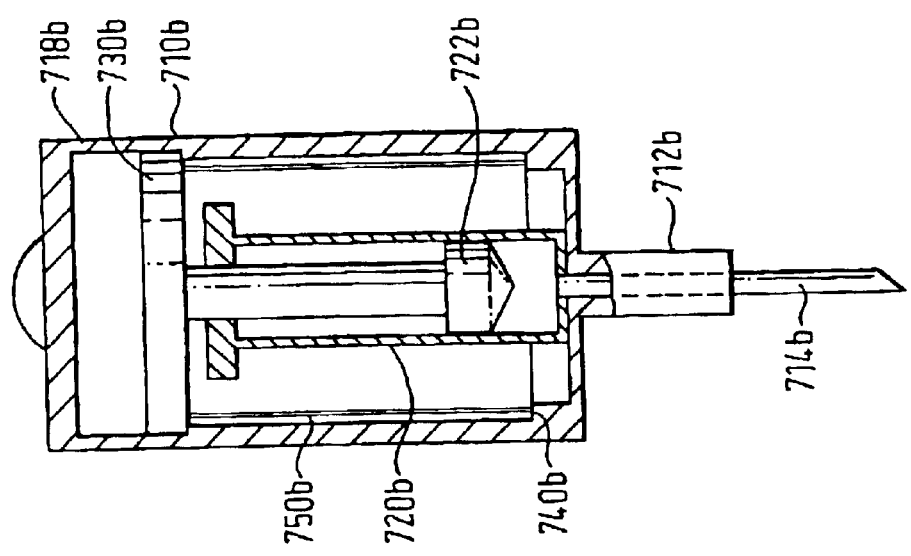
Figure 8A:
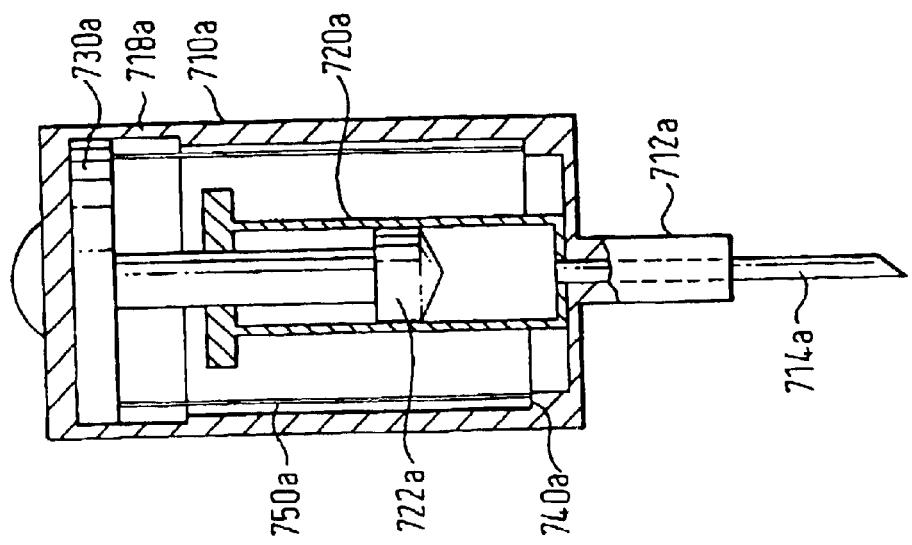

FIGS. 8a, 8b and 8c show schematic representations of a syringe for the delivery of medicament by injection in the rest, fire and retract positions respectively. The syringe comprises a hollow tubular barrel housing 710a–c defining a medicament chamber 720a–c. A dispensing outlet 712a–c leads laterally from the closed end of the chamber 720a–c. Connecting to outlet 712a–c there is provided hollow needle 714a–c through which medicament is dispensed.

The medicament chamber 720a–c has a drug mechanism 722a–c in the form of a plunger rod. The plunger rod 722a–c is movable within the chamber 720a–c to vary the volume thereof and hence, to expel any medicament preparation contained therein (generally in solution form) through the outlet 712a–c to the hollow needle 714a–c. It will thus, be appreciated that dispensing of the medicament requires the plunger 722a–c to be depressed to dispense medicament into the outlet 712a–c and thence to the hollow needle 714a–c through which it is injectable through the skin of a patient.

It may be seen that the upper part 724a–c of the plunger 722a–c is received by actuator seat 730a–c. The actuator seat 730a–c is slidably movable within the housing 710a–c along track 718a–c cut it into the wall of the housing 710a–c. Shape memory alloy wire 750a–c connects actuator seat 730a–c to a fixed anchor position 740a–c at the base of the housing 710a–c. The wire 750a–c comprises a nickel-titanium alloy which contracts in response to the flow of electrical current therethrough. It may thus, be appreciated that when electrical current is passed through the wire 750a–c the actuator seat 730a–c and hence the plunger 722a–c will be drawn down towards the fixed anchor position 740a–c as the wire 750a–c contracts. Actuation of the plunger dispensing mechanism 722a–c and dispensing of the medicament through the outlet 712a–c and hollow needle 714a–c will thereby result.

FIGS. 9a and 9b illustrate an active dry powder reservoir inhaler herein. The inhaler housing 810 comprises a powder metering and transport system comprising a powder reservoir 815, a metered dose plate 816 having a metering cup 817 and a transport coupling in the form of a nickel-titanium shape memory alloy (SMA) wire assembly 818.

The inhaler housing 810 further comprises an aerosolisation system comprising an aerosol container 820 having a valve dispensing mechanism 822 in the form of a slide valve. The aerosol container 820 comprises a liquefied gas such as liquefied air or carbon dioxide. Valve stem 824 connects with aerosolisation block 814. It may be seen that in the dispensing position (FIG. 9b), the block 814 communicates with the metering cup 817 such that when a 'puff' of air of gas is released from the aerosol container 820 it will act to aerosolise a metered powder dose in the metering cup 817. It may be seen that the upper part of the aerosol container 820 is received by container seat 830. The container seat 830 is slidably movable within the housing 810. A second length of shape memory alloy wire 850 connects the container seat 830 to an anchor position 840 on the inhaler housing. The wire 850 comprises a shape memory alloy which contracts in response to the flow of electrical current therethrough.

The inhaler is breath operated such that as the patient inhales the power supply 862 (as controlled by an electronic control system, not shown) sends an electrical current through the SMA wire assembly 818. The SMA wire assembly 818 heats and contracts and draws the metered dose plate 816 containing a metered dose in the metering cup 817 thereof away from the powder reservoir 815 to the aerosolisation block 824 for aerosolisation. Electrical current is then passed through the second shape memory alloy wire 850 which contracts such as to draw the container seat 830 towards the anchor position 840. Actuation of the valve dispensing mechanism 822 and aerosolisation of the powder medicament dose thereby results.

In alternative embodiments, the powder metering and transport system and the aerosolisation system may be actuable through a coupled SMA wire assembly. For example, the SMA wire assembly may sequentially actuate metering, transport and aerosolisation.

It may be appreciated that any of the parts of the dispenser or actuator which contact the medicament suspension may be coated with materials such as fluoropolymer materials (e.g. PTFE or FEP) which reduce the tendency of medicament to adhere thereto. Any movable parts may also have coatings applied thereto which enhance their desired movement characteristics. Frictional coatings may therefore be applied to enhance frictional contact and lubricants (e.g. silicone oil) used to reduce frictional contact as necessary.

The medicament dispenser of the invention is suitable for dispensing medicament, particularly for the treatment of respiratory disorders such as asthma and chronic obstructive pulmonary disease (COPD).

Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (eg s the sodium salt), ketotifen or nedocromil (eg as the sodium salt); anti-infectives e.g., cephalosporins, penicillins, streptomycin, sulphonamides, tetracyclines and pentamidine; antihistamines, e.g., methapyrilene; anti-inflammatories, e.g., beclomethasone (eg as the dipropionate ester), fluticasone (eg as the propionate ester), flunisolide, budesonide, rofleponide, mometasone eg as the furoate ester); ciclesonide, triamcinolone (eg as the acetonide) or 6α, 9α-difluoro-11β hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (eg as free base or sulphate), salmeterol (eg as xinafoate), ephedrine, adrenaline, fenoterol (eg as hydrobromide), formoterol (eg as fumarate), isoprenaline, metaproterenol, phenylephrine, phenylpropanolamine, pirbuterol (eg as acetate), reproterol (eg as hydrochloride), rimiterol, terbutaline (eg as sulphate), isoetharine, tulobuterol or 4-hydroxy-7-[2-[[2-[[3-(2-phenylethoxy)propyl]sulfonyl]ethyl]amino]ethyl-2(3H) benzothiazolone; adenosine 2a agonists, eg 2R,3R,4S,5R)-2-[6-Amino-2-(1S-hydroxymethyl -2-phenyl-ethylamino)-purin-9-yl]-5-(2-ethyl-2H-tetrazol-5-yl)-tetrahydro-furan -3,4-diol (e.g. as maleate); $\alpha_4$ integrin inhibitors eg (2S)-3-[4-({[4-(aminocarbonyl) -1-piperidinyl]carbonyl}oxy) phenyl]-2-[((2S)-4-methyl-2-{[2-(2-methylphenoxy) acetyl] amino}pentanoyl)amino] propanoic acid (e.g as free acid or potassium salt), diuretics, e.g., amiloride; anticholinergics, e.g., ipratropium (eg as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (eg as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt).

A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include, by way of example and without limitation, one or more of the following claims:

What is claimed is:

1. A medicament dispenser comprising
   a housing;
   a medicament container having a dispensing mechanism;
   a container seat which receives the container;
   an anchor station on the housing or connecting therewith; and
   a coupling which extends from said container seat to said anchor station to couple said container seat to said anchor station,
   wherein the coupling is reversibly contractible in response to the application of non-mechanical energy thereto, wherein said container seat is moveable relative to said anchor station to cause actuation of said dispensing mechanism, and wherein the coupling is adapted in use to contract on application of non-mechanical energy thereto so as to move said container seat relative to said anchor station to actuate said dispensing mechanism.

2. A medicament dispenser comprising
   a medicament container having a dispensing mechanism;
   a container seat which receives the container;
   a dispenser seat which receives dispensing mechanism; and
   a coupling which extends from said container seat to said dispenser seat to couple said container seat to said dispenser seat,
   wherein the coupling is reversibly contractible in response to the application of non-mechanical energy thereto, wherein said container seat is moveable relative to said dispenser seat to cause actuation of said dispensing mechanism, and wherein the coupling is adapted in use to contract on application of non-mechanical energy thereto so as to move said container seat relative to said dispenser seat to actuate said dispensing mechanism.

3. A medicament dispenser comprising
   a housing;
   a medicament container containing medicament for release from the dispenser;
   a metering mechanism for metering a dose of said medicament from said medicament container to a predetermined position in said dispenser, an aerosol container having a dispensing mechanism for dispensing gas from said aerosol container to said predetermined position to energise a dose of said medicament thereat;
   a container seat which receives the aerosol container;
   an anchor station on the housing or connecting therewith; and
   a coupling extending from said container seat to said anchor station to couple said container seat to said anchor station,
   wherein the coupling is reversibly contractible in response to the application of non-mechanical energy thereto, wherein said container seat is movable relative to said anchor station to cause actuation of said dispensing mechanism, and wherein the coupling is adapted in use to contract on application of said non-mechanical energy thereto so as to move said container seat relative to said anchor station to actuate said dispensing mechanism.

4. A medicament dispenser according to claim 1, wherein the dispensing mechanism is selected from the group consisting of a valve, pump or plunger mechanism.

5. A medicament dispenser according to claim 1, wherein the dispensing mechanism comprises a metering mechanism.

6. A medicament dispenser according to claim 1, additionally comprising a reset mechanism for resetting the dispensing mechanism after actuation thereof.

7. A medicament dispenser according to claim 6, wherein the reset mechanism comprises a reset coupling which is reversibly deformable in response to the application of non-mechanical energy thereto.

8. A medicament dispenser according to claim 1, wherein said non-mechanical energy comprises electric current flow through the coupling.

9. A medicament dispenser according to claim 1, wherein the coupling comprises a wire, strip, coil or tube.

10. A medicament dispenser according to claim 9, wherein the coupling comprises multiple wires, strips, coils or tubes.

11. A medicament dispenser according to claim 1, wherein the coupling comprises one or more wires which contract in response to the application of non-mechanical energy thereto.

12. A medicament dispenser according to claim 11, wherein the coupling exhibits a degree of contraction of from 2% to 8% on application of non-mechanical energy thereto.

13. A medicament dispenser according to claim 12, wherein the coupling comprises an alloy which undergoes a phase transition on application of non-mechanical energy thereto.

14. A medicament dispenser according to claim 13, wherein said alloy is a nickel-titanium alloy.

15. A medicament dispenser according to claim 14, wherein said nickel-titanium alloy comprises from 5% to 95% nickel by weight and from 95% to 5% titanium by weight, preferably from 20% to 80% nickel by weight and from 80% to 20% titanium by weight.

16. A medicament dispenser according to claim 14, wherein said nickel-titanium alloy additionally comprises copper, niobium or any mixtures thereof.

17. A medicament dispenser according to claim 13, wherein the alloy is a copper-zink-aluminium alloy or a copper-aluminium-nickel alloy.

18. A medicament dispenser according to claim 13, wherein the alloy has the composition defined as $Ni_{65-x-y}Mn_{20}+xGa_{15}+y$, where x is between 3 atomic % and 15 atomic % and y is between 3 atomic % and 12 atomic %.

19. A medicament dispenser according to claim 13, wherein the alloy has the composition defined as $(Ni_aFe_bCo_c)_{65-x-y}(Mn_dFe_eCo_f)_{20}+x(Ga_gSi_hAl_i)_{15}+y$, where x is between 3 atomic % and 15 atomic % and y is between 3 atomic % and 12 atomic %, and where a+b+c=1, where d+e+f=1, and g+h+i=1.

20. A medicament dispenser according to claim 13, wherein the alloy comprises an ion-exchange polymer composite.

21. A medicament dispenser according to claim 13, wherein the alloy comprises a contractile polymer.

22. A medicament dispenser according to claim 11, wherein said one or more wires have a diameter from 30 to 400 micrometers, preferably from 50 to 150 micrometers.

23. A medicament dispenser according to claim 11, wherein the coupling comprises from two to twenty, preferably six to twelve wires which contract in response to heating or application of a magnetic field thereto.

24. A medicament dispenser according to claim 1, wherein said strip comprises multiple layers of different metals.

25. A medicament dispenser according to claim 24, wherein the strip comprises a bimetallic strip.

26. A medicament dispenser according to claim 24, wherein the strip comprises at least one piezoelectric material.

27. A medicament dispenser according to claim 1, wherein the coupling is deformable in response to heating arising from electrical current flow in the range from 0.01 A to 100 A, preferably from 0.1 A to 5 A.

28. A medicament dispenser according to claim 1, wherein the coupling is deformable in response to a magnetic field of from 0.01 to 100 Tesla.

29. A medicament dispenser according to claim 1, additionally comprising an electrical energy source.

30. A medicament dispenser according to claim 29, wherein said electrical energy source comprises a voltaic cell or battery of voltaic cells.

31. A medicament dispenser according to claim 30, wherein said voltaic cell or battery of voltaic cells is rechargeable.

32. A medicament dispenser according to claim 29, wherein said electrical energy source comprises a photovoltaic cell or battery of photovoltaic cells.

33. A medicament dispenser according to claim 29, wherein said electrical energy source comprises a converter for converting mechanical energy into electrical energy.

34. A medicament dispenser according to claim 29, additionally comprising a controller for controlling the amount of electrical current flow through the coupling or to an electromagnet to provide a magnetic field.

35. A medicament dispenser according to claim 29, additionally comprising a timer for controlling the duration of electrical current flow through the coupling or to an electromagnet to provide a magnetic field.

36. A medicament dispenser according to claim 29 additionally comprising a local electrical energy store.

37. A medicament dispenser according to claim 1, wherein said medicament container is a medicament aerosol container.

38. A medicament dispenser according to claim 37, wherein said medicament aerosol container comprises a suspension or a medicament in a propellant.

39. A medicament dispenser according to claim 38, wherein, said propellant comprises liquefied HFA134a HFA-227, helium or carbon dioxide.

40. A medicament dispenser according to claim 39, wherein said medicament aerosol container comprises a solution of a medicament in a solvent.

41. A medicament dispenser according to claim 37, wherein said aerosol container comprises a compressed air or gas and the medicament container comprises medicament in dry powder form.

42. A medicament dispenser according to claim 38, wherein the medicament is selected from the group consisting of albuterol, salmeterol, fluticasone propionate, beclomethasone dipropionate, salts or solvates thereof and any mixture thereof.

43. A medicament dispenser according to claim 4, wherein the valve is a slide valve.

44. A medicament dispenser according to claim 4, wherein the valve is a metering valve.

45. A medicament dispenser according to claim 1, wherein the container seat is shaped for snug receipt of the base of the medicament container or aerosol container.

46. A medicament dispenser according to claim 2, wherein the dispenser seat is shaped for snug receipt of the tip of the dispensing mechanism.

47. A medicament dispenser according to claim 46, wherein the dispenser seat is further shaped to support the walls of the medicament container or aerosol container.

48. A medicament dispenser according to claim 47, wherein the container seat and dispenser seat in combination form a cradle for the medicament container or aerosol container.

49. A medicament dispenser according to claim 2, wherein the container seat and dispenser seat comprise electrically conducting material and the medicament container or aerosol container is electrically insulated therefrom.

50. A medicament dispenser according to claim 49, wherein the dispensing mechanism comprises an electrically insulating material.

51. A medicament dispenser according to claim 50, wherein the dispensing mechanism comprises an electrically conducting material and an insulator is provided between the dispensing mechanism and the dispenser seat.

52. A medicament dispenser according to claim 1, wherein flow of electrical current through the coupling and hence, actuation of the dispensing mechanism is responsive to a patient-actuable trigger.

53. A medicament dispenser according to claim 52, wherein said trigger comprises a button, switch or lever arrangement.

54. A medicament dispenser according to claim 1, in the form of an inhaler for the delivery of inhalable medicament.

55. A medicament dispenser according to claim 54, wherein heating arising from flow of electrical current through the coupling and hence, actuation of the dispensing mechanism is responsive to a patient-actuable trigger comprising a sensor which senses the breath of a patient.

56. A medicament dispenser according to claim 55, wherein said sensor comprises a breath-movable element which is movable in response to the breath of a patient.

57. A medicament dispenser according to claim 56, wherein said breath-movable element is selected from the group consisting of a vane, a sail, a piston, a diaphragm and an impeller.

58. A medicament dispenser according to claim 55, wherein said sensor comprises a pressure sensor for sensing the pressure profile associated with the breath of a patient.

59. A medicament dispenser according to claim 55, wherein said sensor comprises an airflow sensor for sensing the airflow profile associated with the breath of a patient.

60. A medicament dispenser according to claim 55, wherein said sensor comprises a temperature sensor for sensing the temperature profile associated with the breath of a patient.

61. A medicament dispenser according to claim 55, wherein said sensor comprises a moisture sensor for sensing the moisture profile associated with the breath of a patient.

62. A medicament dispenser according to claim 55, wherein said sensor comprises a gas sensor for sensing the oxygen or carbon dioxide profile associated with the breath of a patient.

63. A medicament dispenser according to claim 54, wherein the coupling is exposable to the airflow arising from inhalation or expiration of the patient to assist in the cooling of the coupling post-actuation of the dispensing mechanism.

64. A medicament dispenser according to claim 1 comprising an actuation counter for counting the number of actuations of the dispensing mechanism or a dose counter for counting the number of doses delivered.

65. A medicament dispenser according to claim 64, wherein the actuation counter is independent of the coupling.

66. A medicament dispenser according to claim 1, comprising a manual override enabling manual actuation of the dispensing mechanism.

67. A medicament dispenser according to claim 1 additionally comprising an electronic control system for controlling the supply of non-mechanical energy to the coupling.

68. A medicament dispenser according to claim 67, wherein the electronic control system is capable of providing pulses of non-mechanical energy to the coupling.

69. A medicament dispenser according to claim 67, wherein the electronic control system is capable of receiving inputs from electronic sensors locatable on the dispenser.

70. A medicament dispenser according to claim 69, additionally comprising an electronic sensor selected from the group consisting of a breath sensor, a shake sensor, a temperature sensor, an infrared sensor and a patient ID Sensor.

71. An actuator for a medicament container having a dispensing mechanism comprising
   a container seat for receipt of the medicament container;
   a dispenser seat for receipt of the dispensing mechanism; and
   a coupling which extends from said container seat to said dispenser seat to couple said container seat to said dispenser seat,
   wherein the coupling is reversibly contractible in response to the application of non-mechanical energy thereto, wherein said container seat is moveable relative to said dispenser seat to move the seats towards and away from one another, relative movement of said container seat towards the dispenser causing, in use, actuation of said dispensing mechanism, and wherein the coupling is adapted in use to contract on application of non-mechanical energy thereto so as to cause relative movement of said container seat towards said dispenser seat.

72. An actuator for a medicament container having a dispensing mechanism comprising
   a housing;
   within said housing, a container seat for receipt of the medicament container;
   on the housing or connecting therewith, an anchor station; and
   a coupling extending from said container seat to said anchor station to couple said container seat anchor station,
   wherein the coupling is reversibly contractable in response to the application of non-mechanical energy thereto, wherein said container seat is moveable relative to said anchor station to move the seat and station towards and away from one another, relative movement of said container seat towards the anchor station causing, in use, actuation of said dispensing mechanism, and wherein the coupling is adapted in use to contract on application of said non-mechanical energy thereto so as to cause relative movement of said container seat towards said anchor station.

73. An actuator according to claim 71, wherein said heating is achievable by electric current flow through the coupling.

74. An actuator according to claim 71, wherein the coupling comprises one or more wires which contract in response to the application of non-mechanical energy thereto.

75. An actuator according to claim 71, wherein said coupling comprises an alloy which undergoes a phase transition on the application of non-machanical energy thereto.

76. An actuator according to claim 75, wherein said alloy is a nickel-titanium alloy.

77. An actuator according to claim 71, additionally comprising an electronic control system for controlling the supply of non-mechanical energy to the coupling.

78. An actuator according to claim 77, wherein the electronic control system is capable of providing pulses of non-mechanical energy to the coupling.

79. An actuator according to claim 77, wherein the electronic control system is capable of receiving inputs, from electronic sensors locatable on the dispenser.

80. An actuator according to claim 79, additionally comprising an electronic sensor selected from the group consisting of a breath sensor, a shake sensor, a temperature sensor, an infrared sensor and a patient ID sensor.

81. Laboratory test apparatus for testing a medicament container having a dispensing mechanism comprising at least one actuator according to claim 71 and a mounting for said at least one actuator.

82. Kit of parts comprising
   a medicament dispenser according to claim 1 in the form of a cartridge; and
   a housing shaped for receipt of said cartridge.

83. A medicament dispenser comprising
   a housing;
   a medicament container having a dispensing mechanism;
   a container seat for receipt of the container;
   an anchor station on the housing or connecting therewith; and
   a coupling between said container seat and said anchor station capable on deformation of moving the container seat relative to the anchor station to actuate the dispensing mechanism, wherein the coupling is reversibly deformable-in response to the application of non-mechanical energy thereto, wherein the coupling comprises one or more wires which contract in response to the application of non-mechanical energy thereto, wherein the coupling exhibits a degree of contraction of from 2% to 8% on application of non-mechanical energy thereto, wherein the coupling comprises an alloy which undergoes a phase transition on application of non-mechanical energy thereto.

84. A medicament dispenser according to claim 83, wherein said alloy is a nickel-titanium alloy.

85. A medicament dispenser according claim 84, wherein said nickel-titanium alloy comprises from 5% to 95% nickel by weight and from 95% to 5% titanium by weight, preferably from 20% to 80% nickel by weight and from 80% to 20% titanium by weight.

86. A medicament dispenser according to claim 84, wherein said nickel-titanium alloy additionally comprises copper, niobium or any mixtures thereof.

87. A medicament dispenser according to claim 83, wherein the alloy is a copper-zinc-aluminium alloy or a copper-aluminium-nickel alloy.

88. A medicament dispenser according to claim 83, wherein the alloy has the composition defined as $Ni_{65-x-y}Mn_{20}+xGa_{15}+y$, where x is between 3 atomic % and 15 atomic % and y is between 3 atomic % and 12 atomic %.

89. A medicament dispenser according to claim 83, wherein the alloy has the composition defined as $(Ni_aFe_bCo_c)_{65-x-y}(Mn_dFe_eCo_f)_{20}+x(Ga_gSi_hAl_i)_{15}+y$, where x is between 3 atomic % and 15 atomic % and y is between 3 atomic % and 12 atomic %, and where a+b+c+32 1, where d+e+f+32 1, and g+h+i=1.

90. A medicament dispenser according to claim 83, wherein the alloy comprises an ion-exchange polymer composite.

91. A medicament dispenser according to claim 83, wherein the alloy comprises a contractile polymer.

92. A medicament dispenser comprising
- a medicament container having a dispensing mechanism;
- a container seat for receipt of the container;
- a dispenser seat for receipt of the dispensing mechanism; and
- a coupling between said container seat and said dispenser seat capable on deformation of moving the container seat relative to the dispenser seat to actuate the dispensing mechanism,
- wherein the coupling is reversibly deformable in response to the application of non-mechanical energy thereto, wherein the container seat and dispenser seat comprise electrically conducting material and the medicament container or aerosol container is electrically insulated therefrom.

93. A medicament dispenser according to claim 92, wherein the dispensing mechanism comprises an electrically insulating material.

94. A medicament dispenser according to claim 93, wherein the dispensing mechanism comprises an electrically conducting material and an insulator is provided between the dispensing mechanism and the dispenser seat.

95. A medicament dispenser in the form of an inhaler for the delivery of inhalable medicament, comprising
- a housing;
- a medicament container having a dispensing mechanism;
- a container seat for receipt of the container;
- an anchor station on the housing or connecting therewith; and
- a coupling between said container seat and said anchor station capable on deformation of moving the container seat relative to the anchor station to actuate the dispensing mechanism,
- wherein heating arising from flow of electrical current through the coupling and hence, actuation of the dispensing mechanism is responsive to a patient-actuable trigger comprising a sensor which senses the breath of a patient, wherein said sensor comprises a moisture sensor for sensing the moisture profile associated with the breath of a patient.

96. A medicament dispenser in the form of an inhaler for the delivery of inhalable medicament, comprising
- a housing;
- a medicament container having a dispensing mechanism;
- a container seat for receipt of the container;
- an anchor station on the housing or connecting therewith; and
- a coupling between said container seat and said anchor station capable on deformation of moving the container seat relative to the anchor station to actuate the dispensing mechanism,
- wherein heating arising from flow of electrical current through the coupling and hence, actuation of the dispensing mechanism is responsive to a patient-actuable trigger comprising a sensor which senses the breath of a patient, wherein said sensor comprises a gas sensor for sensing the oxygen or carbon dioxide profile associated with the breath of a patient.

97. An actuator for a medicament container having a dispensing mechanism comprising
- a container seat for receipt of the medicament container;
- a dispenser seat for receipt of the dispensing mechanism; and
- a coupling between said container seat and said dispenser seat capable on deformation of moving the container seat relative to the dispenser seat to actuate the dispensing mechanism,
- wherein the coupling is reversibly deformable in response to the application of non-mechanical energy thereto, wherein said coupling comprises an alloy which undergoes a phase transition on the application of non-mechanical energy thereto.

98. An actuator according to claim 97, wherein said alloy is a nickel-titanium alloy.

* * * * *